US012661131B1

(12) United States Patent
 Simonson

(10) Patent No.: US 12,661,131 B1
(45) **Date of Patent: \*Jun. 23, 2026**

(54) METHOD AND APPARATUS FOR DIRECTIONAL GUIDANCE IN THE PERFORMANCE OF A PARTIAL VERTEBRECTOMY WITHIN A CERVICAL SPINE

(71) Applicant: Robert E. Simonson, Boca Raton, FL (US)

(72) Inventor: Robert E. Simonson, Boca Raton, FL (US)

( \* ) Notice: Subject to any disclaimer, the term of this patent is extended or adjusted under 35 U.S.C. 154(b) by 0 days.

This patent is subject to a terminal disclaimer.

(21) Appl. No.: 19/385,872

(22) Filed: Nov. 11, 2025

Related U.S. Application Data

(60) Continuation of application No. 19/036,488, filed on Jan. 24, 2025, now Pat. No. 12,485,016, which is a division of application No. 18/795,320, filed on Aug. 6, 2024, now Pat. No. 12,232,971.

(51) Int. Cl.
 *A61F 2/44* (2006.01)
 *A61B 17/17* (2006.01)
 *A61B 90/98* (2016.01)
 *A61B 17/00* (2006.01)

(52) U.S. Cl.
 CPC ...... *A61B 17/1757* (2013.01); *A61B 17/1707* (2013.01); *A61B 90/98* (2016.02); *A61F 2/44* (2013.01); *A61B 2017/0023* (2013.01)

(58) Field of Classification Search
 CPC .............................. A61F 2/44; A61B 17/1757
 See application file for complete search history.

(56) References Cited

U.S. PATENT DOCUMENTS

| | | | |
|---|---|---|---|
| 4,341,206 | A | 7/1982 | Perett et al. |
| 5,015,247 | A | 5/1991 | Michelson |
| 5,180,382 | A | 1/1993 | Frigg et al. |
| 5,246,458 | A | 9/1993 | Graham |
| 5,324,290 | A | 6/1994 | Zdeblick |
| 5,364,399 | A | 11/1994 | Lowery et al. |

(Continued)

FOREIGN PATENT DOCUMENTS

| | | | | |
|---|---|---|---|---|
| WO | 199804202 | A1 | 2/1998 | |
| WO | WO-9804202 | * | 2/1998 | ......... A61B 17/1757 |
| WO | 2010063111 | A1 | 6/2010 | |

OTHER PUBLICATIONS

Stryker Corporation, "FDA 510(k) Summary for VertaPlex HV Radiopaque Bone Cement", FDA, Mar. 27, 2015 [Retrieved on Aug. 8, 2025], 6 pages, Retrieved from the Internet: <https://www.accessdata.fda.gov/cdrh_docs/pdf15/K150582.pdf> (Year: 2015).*

(Continued)

*Primary Examiner* — Christian A Sevilla
(74) *Attorney, Agent, or Firm* — Weisberg I.P. Law, P.A.

(57) ABSTRACT

A method of providing a guidance device for guiding a bone removal instrument for the removal of bone from a cervical vertebra and providing a vertebral body replacement device for placement into a void in a cervical spine between two endplates of a single vertebra during the course of an anterior spinal surgical procedure upon the cervical spine wherein the vertebral body replacement device has been given a PLR product code from the Food and Drug Administration (FDA).

30 Claims, 9 Drawing Sheets

(56)                References Cited

U.S. PATENT DOCUMENTS

| | | | |
|---|---|---|---|
| 5,549,612 | A | 8/1996 | Yapp |
| 5,591,235 | A | 1/1997 | Kuslich |
| 6,248,110 | B1 | 6/2001 | Reiley |
| 6,419,705 | B1 | 7/2002 | Erickson |
| 6,436,102 | B1 | 8/2002 | Ralph et al. |
| 6,679,886 | B2 | 1/2004 | Weikel et al. |
| 7,094,239 | B1 | 8/2006 | Michelson |
| 7,128,760 | B2 | 10/2006 | Michelson |
| 7,160,304 | B2 | 1/2007 | Michelson |
| 7,226,481 | B2 | 6/2007 | Kuslich |
| 7,303,565 | B2 | 12/2007 | Buttermann |
| 7,803,188 | B2 | 9/2010 | Justis et al. |
| 7,867,263 | B2 | 1/2011 | Lowry |
| 7,905,885 | B2 | 3/2011 | Johnson et al. |
| 8,163,021 | B2 | 4/2012 | Lowry |
| 8,425,569 | B2 | 4/2013 | O'Farrell |
| 8,879,934 | B2 | 11/2014 | Kameda |
| 8,979,934 | B2 | 3/2015 | Kirshman |
| 9,044,338 | B2 | 6/2015 | Schaller |
| 9,962,166 | B1 * | 5/2018 | Sachs ................. A61F 2/30744 |
| 10,064,735 | B1 | 9/2018 | Simonson et al. |
| 10,137,000 | B1 | 11/2018 | Simonson et al. |
| 10,751,192 | B1 | 8/2020 | Simonson et al. |
| 11,000,290 | B1 | 5/2021 | Sachs et al. |
| 11,083,593 | B1 * | 8/2021 | Simonson ............. A61F 2/4611 |
| 11,523,912 | B1 | 12/2022 | Simonson et al. |
| 11,766,338 | B1 | 9/2023 | Simonson |
| 11,857,431 | B1 | 1/2024 | Simonson |
| 11,925,564 | B1 | 3/2024 | Simonson |
| 11,944,326 | B2 | 4/2024 | Morris et al. |
| 12,485,016 | B1 * | 12/2025 | Simonson ............. A61B 90/98 |
| 2001/0056302 | A1 | 12/2001 | Boyer et al. |
| 2002/0068974 | A1 | 6/2002 | Kuslich |
| 2003/0004575 | A1 | 1/2003 | Erickson |
| 2003/0065396 | A1 | 4/2003 | Michelson |
| 2003/0125747 | A1 | 7/2003 | Sproul |
| 2003/0135217 | A1 * | 7/2003 | Buttermann ....... A61B 17/1757 |
| | | | 606/79 |
| 2003/0181982 | A1 | 9/2003 | Kuslich |
| 2003/0195518 | A1 | 10/2003 | Cragg |
| 2006/0111714 | A1 | 5/2006 | Foley |
| 2008/0154304 | A1 * | 6/2008 | Crawford ........... A61B 17/8819 |
| | | | 206/572 |
| 2009/0076555 | A1 | 3/2009 | Lowry et al. |
| 2009/0240334 | A1 | 9/2009 | Richelsoph |
| 2016/0374819 | A1 | 12/2016 | Ballard |
| 2024/0245411 | A1 | 7/2024 | Morris et al. |

OTHER PUBLICATIONS

European Spine Journal, Jan. 3, 2007, Gun Choi et al.
Brochure—Medtronic Sofamor Danek—"Atlantis™ Anterior Cervical Plate System Surgical Technique" by Volker K. H. Sonntag, M.D., Barrow Neurological Institute, Regis W. Haid, Jr., M.D., Emory Clinic, Stephen M. Papadopoulos, Barrow Neurological Institute, M.D.
510(k) premarket notification of intent to market and device description of Skyline® Anterior Cervical Plate System, Uniplate® Anterior Cervical Plate System, and Uniplate® 2 Anterior Cervical Plate System, Jul. 25, 2013, Submitted by Medos International Sàrl, Switzerland, DePuy Spine, Inc., Raynham, Massachusetts and Kirsten Lehmuller, Raynham, Massachusetts.
Surgical Technique & Ordering Information, Anterior Cervical Plate System for The Skyline ACP System Description, DePuy Spine Inc., a Johnson & Johnson company, designing surgeons Curtis A. Dickman, MD, Barrow Neurological Institute, Jeffrey S. Fischgrund, MD, William Beaumont Hospital, Michael G. Fehlings, MD, Ph.D., FRCSC, University of Toronto, Michael W. Groff, MD, Indiana University, Robert F. Heary, MD, UMDNJ, New Jersey Medical School, Mark E. Shaffrey, MD, University of Virginia Health System, 2010, pp. 1-24.
Kim, Jin-Sung et al.; Modified transcorporeal anterior cervical microforaminotomy assisted by O-arm-based navigation: a technical case report; Eur Spine J (2011) 20 (Suppl 2):s147-S152; DOI 10.1007/s00586-010-1454-2; 2011, consisting of 6 pages.
Sonntag, Volker K.H., Dr. et al.; Atlantis Anterior Cervical Plate System Surgical Technique; Medtronic Sofamor Daanek; 2002, consisting of 39 pages.
Globus Medical, Crossway Transcorporeal MicroDecompression (TCMD), 2026, consisting of 7 pages.
Globus Medical, Crossway Allograft Spacer, EXT-238 (R00), Apr. 2024, consisting of 2 pages.
Lowry, D., et al., Clinical Outcomes After Cervical Transcorporeal Microdecompression and Vertebral Body Access Channel Repair, International Journal of Spine Surgery, 2015, vol. 9, Article 10, consisting of 8 pages.
Rodenhouse, A., 510(k) Summary, Pursuant to 21 CFR 807.92c, Device Information: Trade Name: Transcorp ACIF System, Common Name: Intervertebral Body Fusion Device, Classification: 21 CFR Section 888.3080, Product Code ODP, Class II, Sep. 10, 2010, consisting of 5 pages.
Truong, T., TransCorp Spine, 510(k) Summary, Pursuant to 21 CFR 807.92c, Device Information: Trade Name: Transcorp ACIF System, Common Name: Intervertebral Body Fusion Device, Classification: 21 CFR Section 888.3080, Product Code ODP, Class II, Jun. 26, 2013, consisting of 6 pages.
Rodenhouse, A., Transcorp, Inc. 510(k) Summary, Pursuant to 21 CFR 807.92c, Device Information: Trade Name: Transcorp TransPlate Anterior Cervical Plate System, Common Name: Spinal Intervertebral Body Fixation Orthosis, Classification: 21 CFR Section 888.3060, Product Code KWQ, Class II, May 20, 2010, consisting of 5 pages.
Rodenhouse, A., 510(k) Summary, Pursuant to 21 CFR 807.92c, Device Information: Trade Name: Transcorp Spinal Access System, Common Name: Rigid Endoscope and Instrument Set, Classification: 21 CFR Section 888.1100, Arthroscope Product Code: HRX, Mar. 29, 2012, consisting of 5 pages.

* cited by examiner

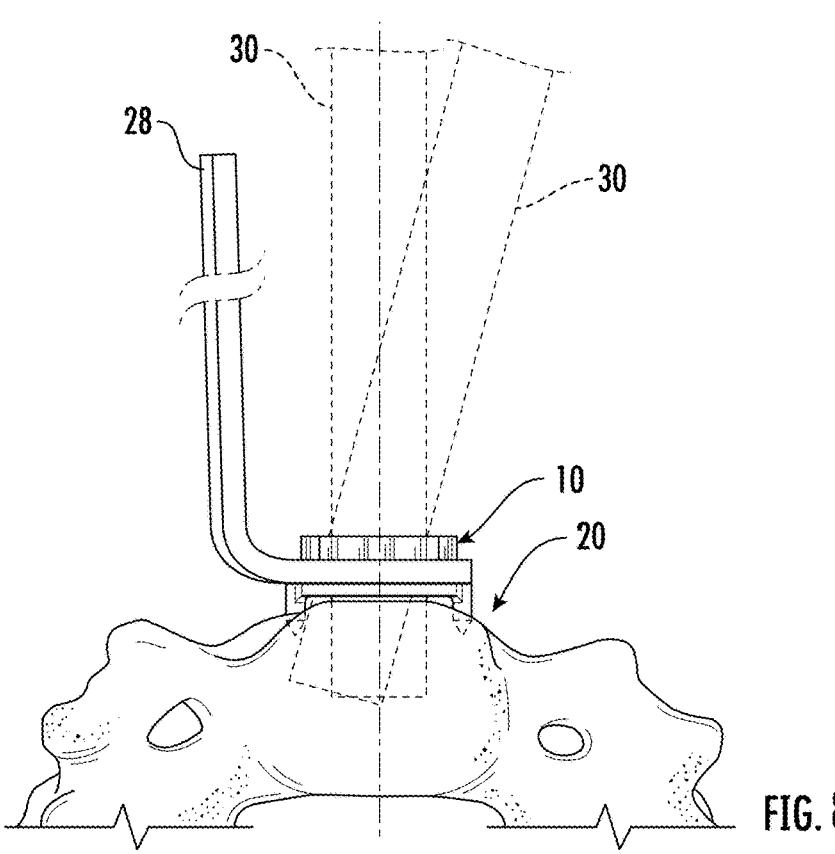
FIG. 8
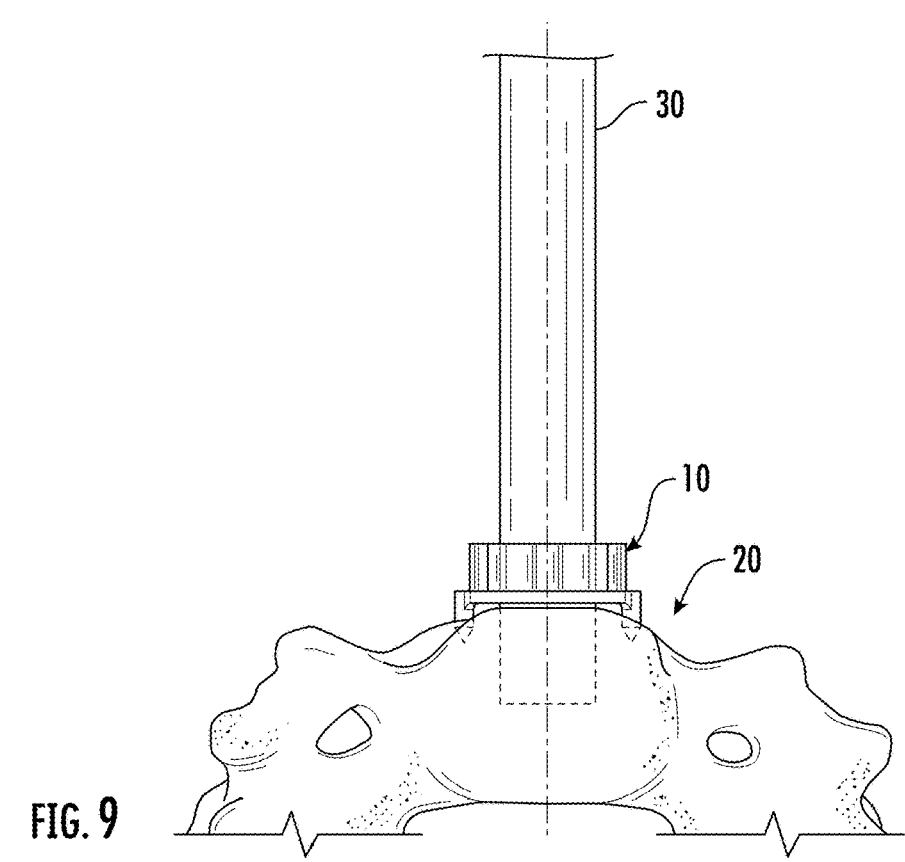
FIG. 9

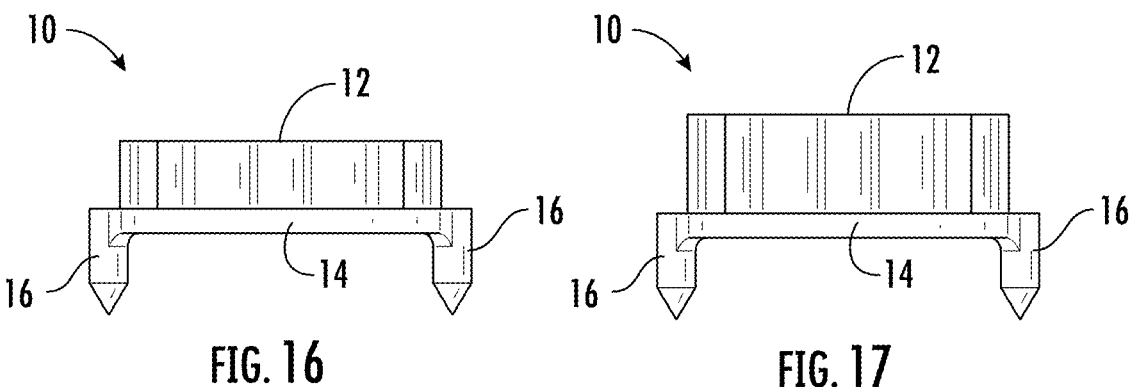
FIG. 16
FIG. 17
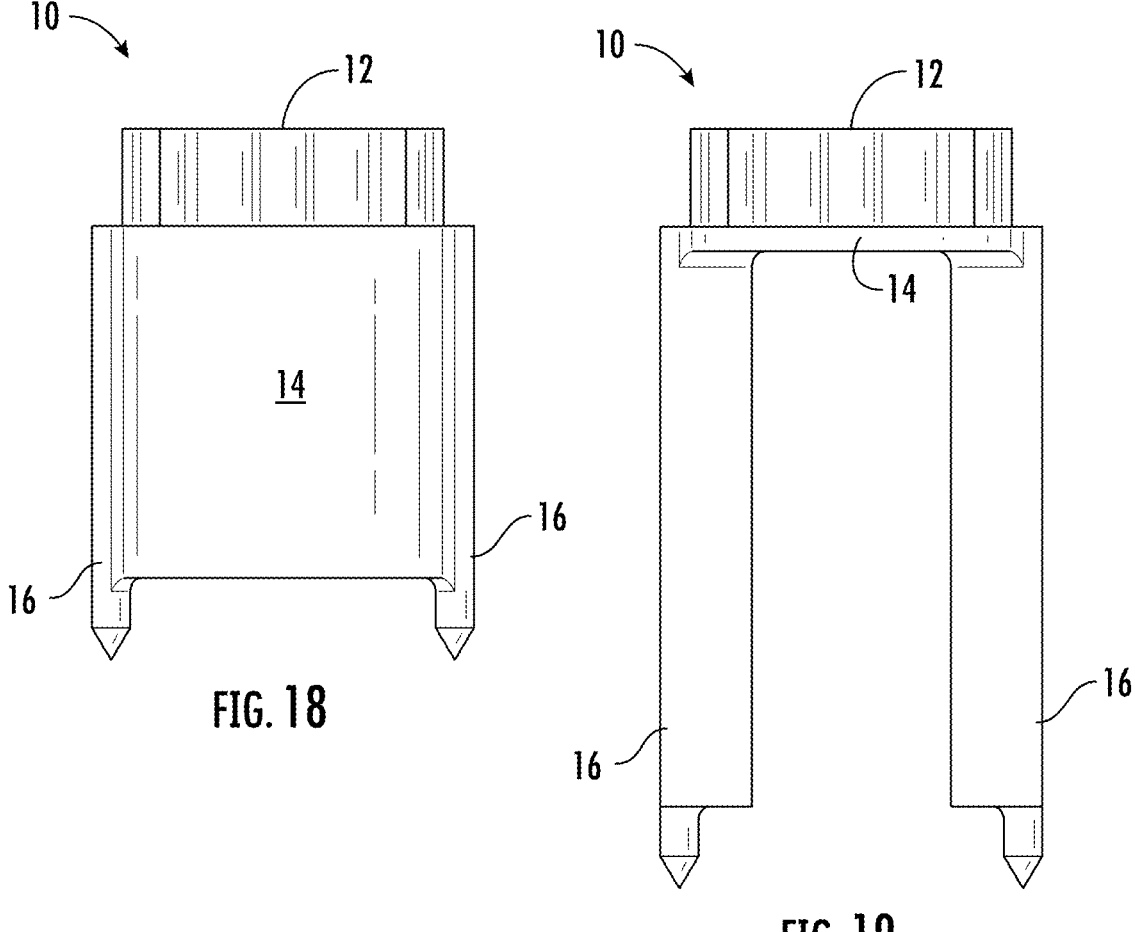
FIG. 18
FIG. 19

METHOD AND APPARATUS FOR DIRECTIONAL GUIDANCE IN THE PERFORMANCE OF A PARTIAL VERTEBRECTOMY WITHIN A CERVICAL SPINE

CROSS-REFERENCE TO RELATED APPLICATIONS

This application is a Continuation Application of U.S. Divisional application Ser. No. 19/036,488, filed Jan. 24, 2025 entitled "METHOD AND APPARATUS FOR DIREC-TIONAL GUIDANCE IN THE PERFORMANCE OF A PARTIAL VERTEBRECTOMY WITHIN A CERVICAL SPINE," which is a Divisional Application of U.S. application Ser. No. 18/795,320, filed Aug. 6, 2024 entitled "METHOD AND APPARATUS FOR DIRECTIONAL GUIDANCE IN THE PERFORMANCE OF A PARTIAL VERTEBRECTOMY WITHIN A CERVICAL SPINE," the entirety of both of which are incorporated herein by reference.

TECHNICAL FIELD

The present disclosure relates to providing a guidance method and apparatus to be used in the performance of a cervical partial vertebrectomy procedure performed during the performance of a surgical procedure upon an anterior cervical spine. The use of the guidance method and apparatus will allow for the reduction in excess bone removal, excess endplate removal and excess intervertebral disc removal.

BACKGROUND

The term "corpectomy" is often used to describe the removal of a vertebral body or corpus. The term "corpectomy" can be used in place of the word vertebrectomy. In common use and as well in this disclosure, the term "vertebrectomy" in the performance of an anterior cervical spinal surgical procedure can be used interchangeably with "corpectomy."

During the performance of an anterior cervical spinal surgery, the term "corpectomy" or "vertebrectomy" means the functional removal of the vertebral body. The anterior portion of a vertebra is primarily made up of a superior vertebral endplate and an inferior vertebral endplate with the mass of the vertebral body in between. When a surgeon has to completely remove a vertebral body including function-ally eliminating one or both of the vertebral endplates, the procedure the surgeon will perform is called a vertebrec-tomy. Due to the need to minimize the time the surgical procedure requires, the surgeon may leave portions of the vertebral body in place if that serves the patient's best interest but functionally the entire vertebral body will be removed. In a partial vertebrectomy, a portion of the verte-bral body is removed but the effort does not attempt full removal. During a partial vertebrectomy standard procedure teaches the removal of one intervertebral disc as well as one of the vertebral endplates and removal of a portion of the vertebral body and then performing a fusion of the remain-ing portion of the vertebral body to the vertebra adjacent to the removed intervertebral disc. Typically, a vertebrectomy includes the removal of two intervertebral discs and a fusion to the two vertebrae adjacent to the removed vertebral body and a partial vertebrectomy includes the removal of one intervertebral disc and a fusion to the one vertebra adjacent to the removed intervertebral disc and significant portion of the removed vertebral body.

The performance of a vertebrectomy or a partial verte-brectomy is associated with gross bone removal from a vertebral body of one or more vertebrae. The method that bone is most often removed is through the use of high-speed bone cutting burs attached to high RPM drill-type devices and removal begins at a superior or inferior vertebral end-plate after the removal of the intervertebral disc adjacent to the vertebra. This is an effective method of bone removal that usually permits bulk removal of bone in a timely manner.

Surgeons have a wide range of preferences as to their preferred instrument to be used in the performance of bone removal. During a partial vertebrectomy surgical procedure, a surgeon may use more than one instrument to remove bone and commonly a surgeon may go back and forth using multiple different instruments. Typical instruments will include, for example, a hand-held trephine, a hand-held drill bit with a handle, a power drill, and a high-speed burr, among other instruments. Therefore the terms "bone removal tool," "bone removal device," or "bone removal instrument" may be used interchangeably throughout this disclosure to recognize whichever instrument the surgeon may select.

Drill guides used to aid in the placement of screw holes and/or through-holes, or used for implant devices for ortho-pedic surgeries are common and such guide devices have been in use for years. Stereotactic guides have been used commonly in neurosurgery for brain biopsies, etc., but direct guidance methods and mechanisms for use in anterior cer-vical partial vertebrectomy procedures have heretofore not been invented.

The following are some of the general challenges and limitations inherent with the surgical approach and exposure associated with a partial vertebrectomy procedure during anterior cervical spine surgery. Stereotactic guidance mechanisms, which may also include what is referred to as "image guidance" with computer assistance, require various types of apparatuses to be attached to or placed around the target bone anatomy and in close proximity to the surgical site. The vertebrae of the anterior cervical spine are com-parably small and anterior cervical vertebrae are accessed by necessarily small surgical openings compared to many other procedures such as open posterior approaches. Surgeons are typically reluctant to expand the surgical exposure for the inclusion of guidance devices beyond the exposure required for the clinical requirements of the surgical procedure itself.

The computer assisted image guidance systems are not direct guidance methods and mechanisms in that they use a "virtual reality" image which is computer generated and appears on a computer screen as a simulation. Although these types of image guidance systems may prove effective for certain surgical procedures, because of the requirement of a reference arc to be attached to bone, or other cumber-some devices, they have not been commonly used in the performance of a partial vertebrectomy procedure in the anterior cervical spine as they are impractical for such a use. In fact, to date, computer-based image guidance systems have failed to be broadly helpful in the performance of a partial vertebrectomy in the cervical spine. Image guidance systems currently have been determined to be too cumber-some, too instrument intensive, too costly, and too time consuming for surgeons to feel comfortable in the use of image guidance systems for the partial vertebrectomy pro-cedure.

Additionally, the medical community has assumed the current methods of performing the anterior cervical partial vertebrectomy procedure are sufficient, and therefore the procedure has been ignored with no attempts to apply minimally disruptive methods to the anterior cervical partial vertebrectomy procedure prior to this disclosure.

Orthopedic-type drill guides are commonly used for placing screw holes, through-holes, or other implant-related holes in the bones of the spine or elsewhere in the skeletal system. No drill guides or any other guides for making specific holes in skeletal structures have been used or designed to be used during the performance of an anterior cervical partial vertebrectomy procedure. Drill guides that are used for the placement of screws for cervical plates, transcorporeal plates, or through holes, or brain biopsy procedures cannot practically be used during the performance of a partial vertebrectomy procedure. The unique aspects of a partial vertebrectomy procedure require a guidance method and associated devices specifically designed for the range of pathologies requiring the performance of the partial vertebrectomy surgical procedure.

For example, transcorporeal cervical spine surgery necessarily creates an access through-hole through a vertebral body and may or may not use a guide. While it is possible that a surgeon performing a partial vertebrectomy procedure may make a hole through a vertebral body if the surgeon or the pathology require it, a through-hole is not a requirement of a partial vertebrectomy procedure while a through-hole is a requirement with a transcorporeal procedure. A transcorporeal drill guide requires making a hole all the way through a vertebral body. The making of a hole through a vertebral body is not necessarily a part of the partial vertebrectomy procedure as it is in a transcorporeal procedure and may be contraindicated is some cases. In other words, a partial vertebrectomy procedure is a procedure that can be performed for a range of indications, several of which do not require the making of a hole through a vertebral body. Therefore, a guide and a method of guidance to be used during a partial vertebrectomy procedure will need to have considerably broader applications to address the defined indications of the partial vertebrectomy procedures and be more versatile than a transcorporeal guide or any other drill guide currently available.

Furthermore, when a guide has been used in conjunction with the drilling of a hole through a vertebral body during a transcorporeal spine surgery procedure, the guide is associated with an implant and maybe even with a transcorporeal bone plate or fixture screwed to the vertebral body. This transcorporeal implant and bone plate may be necessary or helpful in every transcorporeal procedure, but it is not necessary or helpful in every partial vertebrectomy procedure. Furthermore, the drilling of a hole during the performance of a transcorporeal procedure is a required surgical step in a surgical procedure and not the procedure in and of itself, whereas the performance of the partial vertebrectomy procedure describes removing a portion of the vertebral body as the surgical procedure, therefore the removal of the bone from the vertebral body may be the actual procedure.

The definition of a partial vertebrectomy is the removal of a part or portion of the vertebral body. Therefore, depending on the individual patient's needs the performance of the bone removal may include the removal of the pathogenic target and allow the surgeon to begin the process of concluding the procedure. A transcorporeal procedure is always creating a pathway as a step to performing a surgical procedure such as a partial discectomy or a foraminotomy etc.

In other words, a partial vertebrectomy is a broader surgical procedure, whereas a transcorporeal procedure using a drill guide as described in prior art limits the use of a guide to only creating a pathway through a vertebral body. While a partial vertebrectomy may also provide access to a target after the removal of bone, the surgical indications for a partial vertebrectomy are far broader than the prior art drill guides described for use in transcorporeal procedures allow for. Furthermore, these prior art transcorporeal drill guides only describe creating a pathway to a target wherein the partial vertebrectomy allowing for broader indications may remove the target when bone removal is performed.

Additionally, as pointed out previously, a transcorporeal procedure and the associated equipment, implants, and guides used in such a procedure are specifically designed only for drilling a specially directed and angled hole through a vertebral body every time and for the performing a procedure through the hole and beyond the vertebral body. The transcorporeal guidance devices and methods that are used necessarily require the inclusion of specific transcorporeal implants, including bone plates and screws which are not designed for use in or associated with the performance of a partial vertebrectomy procedure.

If a drill guide is associated with the dimensions and specifications of a specific implant device, it is necessarily configured to prepare the location in the bone for the specific implant device. A guide associated and designed to be mated to a specific implant is generally unsuitable for use without that specific implant. All engineering regarding patient safety and recovery would have been performed with the consideration of the implant aiding in the recovery and structural support to the bone. This is helpful if the surgeon is using that specific implant device for that specific indication but it is limited to the configuration and use of that implant device. If an implant device is to be used in a different procedure than the procedure it has been designed for, it must first be analyzed by Food and Drug Administration (FDA) protocols for patient safety and efficacy before use. A device must demonstrate it is safe and effective for all of the indications of the other procedure. In other words, a transcorporeal guidance device may be safe and effective for a transcorporeal procedure but that does not make it safe and effective for the broad indications of a partial vertebrectomy procedure. In fact, as the guidance device of a transcorporeal procedure which has a requirement of an implant, has a much narrower application regarding indications for use; it is obvious to one schooled in the art of neuro and orthopedic spine surgery that there is not enough overlap of the indications for use for the use of a transcorporeal guidance device to be expected to perform the broader indications for use as required of a partial vertebrectomy procedure with or without an implant.

A surgical procedure is formalized with a name, a billing code, a regulatory description, and often a series of steps that are recognized as being part of or a main goal of the surgical procedure. As an example, to perform an anterior cervical discectomy and fusion procedure, often referred to as an ACDF, a drill guide may be used that is designed by a manufacturer to interface with the manufacturer's cervical plate to drill one or more screw holes in the trajectory and depth required by the plate and as specified by the manufacturer of the plate. At the surgeon's discretion, these screw holes may be drilled into the vertebral body (unicortical) or drilled all the way through the vertebral body (bicortical). In this example, the procedure would be an Anterior Cervical Discectomy and Fusion and the procedure would be described and billed as such. The surgeon may add a billing code for placing a cervical plate. Thus, the drilling of the screw hole for the placement of a screw is not the procedure itself, but instead is a surgical step within the procedure. The step of drilling a hole into or through a vertebra for a screw is entirely different than performing a partial vertebrectomy procedure.

For the reasons stated above and more, it is clear that there is not a suitable guide and guidance method for partial vertebrectomy procedures and this places the patient at a disadvantage. Currently, partial vertebrectomy procedures are performed by freehand and the approach to the target is indirect with wide sweeping bone removal techniques. The methods and devices of this disclosure intend to remedy these shortcomings.

SUMMARY

The guidance method and devices of this disclosure are to be used to assist in the planning and the performance of the removal of bone from a vertebral corpus of the cervical spine during the performance of a partial vertebrectomy anterior cervical surgical procedure.

A transcorporeal guide device is singularly designed for a specific type of hole created through a vertebra. A transcorporeal hole is a hole through a vertebral body wherein the terminus of the hole in the posterior surface of the vertebral body is in proximity to a site in need of a medical procedure. A transcorporeal drill hole must necessarily go completely through a vertebral body and the associated equipment is designed to that specific end along with simultaneously preparing the site to receive the implant. The method and guidance devices of the present disclosure may be used to create a hole through the vertebral body if that is what the surgeon determines is in the patient's best interest. The methods and guidance devices of this disclosure may also be used in procedures or portions of procedures that do not pass all the way through a vertebral body and may or may not require an implant. As will be described in greater detail throughout this disclosure, the partial vertebrectomy procedure is used for a broad range of pathologies that may impact a patient. Therefore, a partial vertebrectomy procedure guidance device must be able to function in more than a singular capacity.

Described throughout this disclosure is an inventive method and inventive apparatus for performing a less disruptive anterior cervical partial vertebrectomy procedure. An anterior cervical partial vertebrectomy is a defined surgical procedure with a number of indications requiring precise removal of portions of a vertebral body. This also means that this is a procedure and not only a surgical step in a portion of a procedure, meaning that the partial vertebrectomy procedure may necessarily require additional steps that are part of a surgical procedure such as anesthesia and a surgical incision and so forth, but the procedure will still be recognized as the performance of a partial vertebrectomy procedure. Furthermore, as described, the partial vertebrectomy procedure can be performed for a variety of reasons, treating patient's various pathologies, and this procedure, like all procedures, can be performed in conjunction with other procedures.

Disclosed herein is a new guidance method and apparatus specifically designed for use during the performance of a partial vertebrectomy procedure in the cervical spine during the course of an anterior cervical spine surgery. Also disclosed herein are associated devices that will permit enhanced and more accurate preoperative planning as well as increased accuracy during the bone removal procedure.

The combined inclusion and disclosure of the improvement in preoperative planning, with the introduction of direct guidance and improved bone removal methods and devices will lead to an overall reduction in the volume of bone unnecessarily removed from the patient.

Disclosed herein is a method of providing a guidance device for guiding a bone removal instrument in the performance of a partial vertebrectomy performed upon a vertebral body of a cervical spine during an anterior spinal surgical procedure where the vertebral endplates of the vertebral body are functionally preserved.

Disclosed herein is a method of performing a pre-operative image study and using the image study to measure the distance and angle from a starting point on a cervical vertebral body to a stopping point and translating the measurements of distance and angle from the pre-operative image study to a guidance device used in the performance of a partial vertebrectomy surgical procedure.

Disclosed herein is a method of providing a guide for the purpose of directionally guiding a bone removal instrument during the performance of an anterior cervical partial vertebrectomy procedure where the void created by the guiding of the bone removal instrument is repaired at least in part with the placement of a vertebral body replacement device that has a PLR product code from the FDA.

Further disclosed herein is the performance of the above-described method where the endplates of the cervical vertebral body receiving the partial vertebrectomy and the adjacent intervertebral discs remain functionally intact.

In accordance with an embodiment of one aspect of the present disclosure, the disclosed method provides for a guidance device for guiding a bone removal instrument for the removal of bone from a cervical vertebra and providing a vertebral body replacement device for placement into a void in the cervical vertebra between two endplates of the cervical vertebra during the course of an anterior spinal surgical procedure upon the cervical spine wherein the vertebral body replacement device has been given a PLR product code from the Food and Drug Administration (FDA).

In accordance with an embodiment of another aspect of the present disclosure, the disclosed method provides a guidance device for the guidance of a bone removal tool in the performance of a partial vertebrectomy procedure and placing a vertebral body replacement device between two vertebral endplates of a single vertebra in a cervical spine. The method includes creating a void between the two endplates of the single vertebra of the cervical spine, and placing the vertebral body replacement device into the void between the two endplates of the single vertebra, wherein the vertebral body replacement device has been given a PLR product code from the Food and Drug Administration (FDA).

In another embodiment of this aspect, the guidance device is part of a series of guidance devices, further comprising selecting at least one guidance device from the series of guidance devices. In another embodiment, the guidance device may contain a single angle or compound angles. In another embodiment, the guidance device comprises a handle feature, wherein the handle feature is a separate instrument and is removable from the guidance device. In another embodiment, the guidance device has a height profile of less than 20 millimeters. In another embodiment, the guidance device has a height profile of less than 15 millimeters. In another embodiment, the guidance device has a height profile of less than 10 millimeters. In another embodiment, the guidance device has a height profile of less than 6 millimeters. In another embodiment, the guidance device is a single use/disposable guidance device.

In accordance with an embodiment of another aspect of the present disclosure, a method of performing a multi-aperture partial vertebrectomy procedure to a vertebral body of a cervical spine during the performance of an anterior cervical spinal surgery using a guidance device is provided. The method comprises creating a first partial vertebrectomy void having an entrance and a terminus region and creating a second partial vertebrectomy void in the same vertebral body of the cervical spine of the first partial vertebrectomy void.

In another embodiment of this aspect, the guidance device is part of a series of guidance devices, further comprising selecting and at least one guidance device from the series of guidance devices. In another embodiment, the guidance device may contain a single angle or compound angles. In another embodiment, the guidance device further comprises a handle feature, wherein the handle feature is a separate instrument and is removable from the guidance device. In another embodiment, the guidance device has a height profile of less than 20 millimeters. In another embodiment, the guidance device has a height profile of less than 15 millimeters. In another embodiment, the guidance device has a height profile of less than 10 millimeters. In another embodiment, the guidance device has a height profile of less than 6 millimeters. In another embodiment, the guidance device is a single use/disposable guidance device. In another embodiment, the guidance device is available by prescription only.

In accordance with an embodiment of another aspect of the present disclosure, a physical guidance device is provided. The physical guidance device is for use in guiding removal of bone from a selected starting point to a selected termination point during the performance of a partial vertebrectomy procedure to a cervical vertebral body wherein the procedure includes the placement of a vertebral body replacement device into a void between the vertebral endplates of a single vertebra of the cervical spine and the vertebral body replacement device has been given a PLR product code from the Food and Drug Administration (FDA).

According to another embodiment of this aspect, the physical guidance device is part of a series of physical guidance devices, and at least one physical guidance device is selected from the series of physical guidance devices. In another embodiment, the guidance device may contain a single angle or compound angles. In another embodiment, the guidance device comprising a handle feature, wherein the handle feature is a separate instrument and is removable from the physical guidance device. In another embodiment, the guidance device has a height profile of less than 20 millimeters. In another embodiment, the guidance device has a height profile of less than 15 millimeters. In another embodiment, the guidance device has a height profile of less than 10 millimeters. In another embodiment, the guidance device has a height profile of less than 6 millimeters. In another embodiment, the physical guidance device is a single use/disposable guidance device. In another embodiment, the physical guidance device further comprises indicia, the indicia providing additional guidance for a user before, during and after removal of bone from the vertebra.

BRIEF DESCRIPTION OF THE DRAWINGS

FIG. 3 is a top view of the physical guidance device of the present disclosure and an anterior or frontal view of the cervical vertebra with an angled void partially through the cervical vertebra;

FIG. 4 is a bottom view of the physical guidance device of the present disclosure and a posterior view of the cervical vertebra with an angled void partially through the cervical vertebra;

FIG. 5 is a top view of the physical guidance device of the present disclosure and an anterior perspective view of the cervical vertebra with an alternately angled void partially through the cervical vertebra;

FIG. 6 is a bottom view of the physical guidance device of the present disclosure and a posterior view of the cervical vertebra with the alternately angled void partially through the cervical vertebra;

FIG. 8 is a is an axial perspective view of the physical guidance device of the present disclosure with a handle showing an angle of insertion;

FIG. 9 is an axial view of the physical guidance device of the present disclosure without a handle;

FIG. 16 is a side view of the physical guidance device of the present disclosure having a first height profile;

FIG. 17 is a side view of the physical guidance device of the present disclosure having a second height profile;

FIG. 18 is a side view of the physical guidance device of the present disclosure having a third height profile;

FIG. 19 is a side view of the physical guidance device of the present disclosure having a fourth height profile.

DETAILED DESCRIPTION

Figure 1:
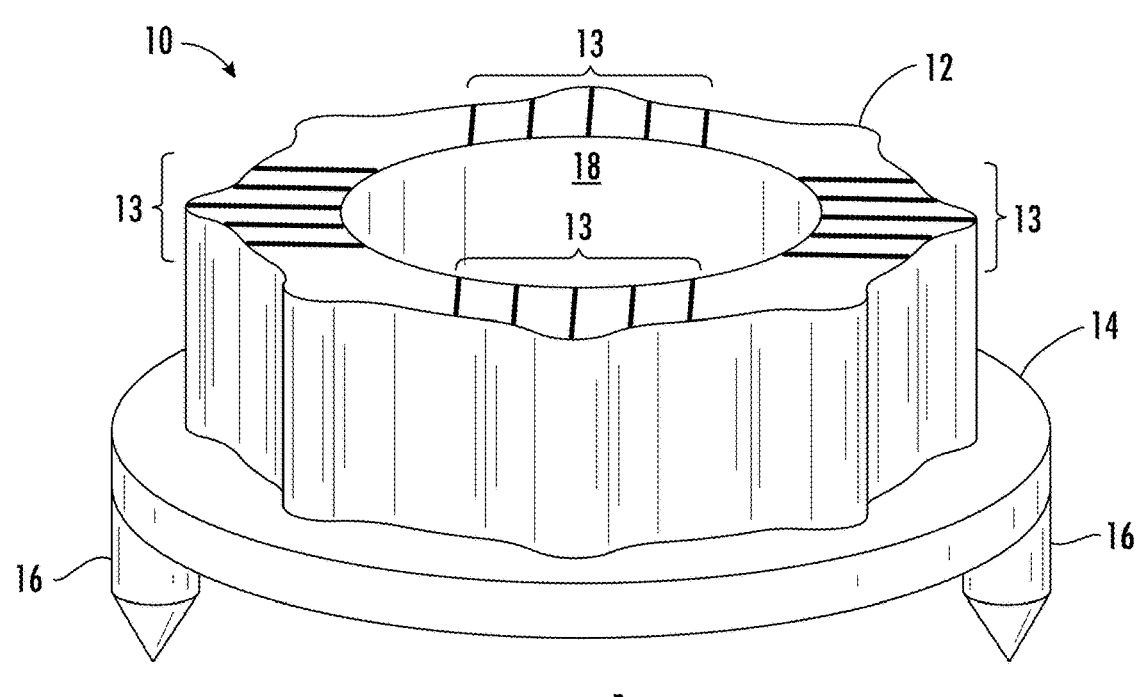
FIG. 1 is a side view of the physical guidance device of the present disclosure.
Figure 2:
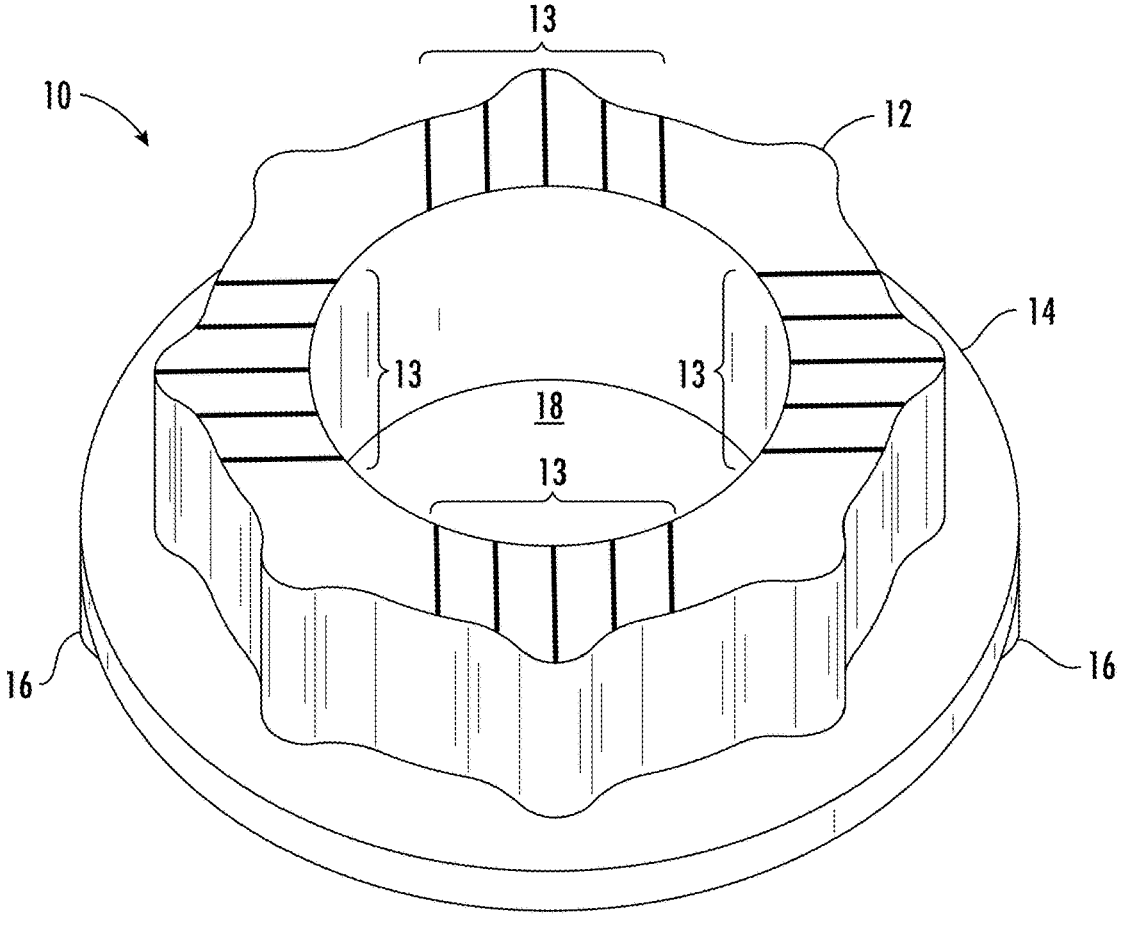
FIG. 2 is a top, perspective view of the physical guidance device of the present disclosure.

Referring now to the figures, there is shown in FIG. 1 a side, perspective view of the physical guidance device 10 of the present disclosure. FIG. 2 shows top, perspective view of physical guidance device 10. As described herein, physical guidance device 10 includes an upper portion 12, with, in some embodiments, indicia or markings 13 thereon, a platform or lower portion 14, and a plurality of legs 16 extending downward from platform 14. Upper portion 12 forms a cylindrical shape with an aperture 18 therein. Aperture 18 is sized to receive and guide a bone removal instrument, as described herein. Although not shown in FIGS. 1 and 2, aperture 18 can be advantageously angled in order to allow guidance device 10 to receive a bone removal instrument and guide the instrument at an angle either partially or completely through the vertebral body. As explained in further detail below, the ability to assist a surgeon in guiding the bone removal instrument through (or partially through) the vertebral body at one or more angles is invaluable in surgical procedures.

FIGS. 1 and 2 show one embodiment where physical guidance device 10 has an irregular outer perimeter. The shape of the outer perimeter of physical guidance device 10 can be designed to receive a handle, which, as discussed herein, can be used to grip and hold physical guidance device 10 and apply downward pressure or other holding functions. It is within the scope of the present disclosure to provide a physical guidance device 10 with various types of dimensions, outer circumferential shapes and contours, to accommodate differently sized bone removal instruments, and/or differently shaped handles.

In some embodiments, the markings 13 on the visible portion of upper portion 12 of guidance device 10 represent indicia to give the surgeon additional flexible guidance if the surgeon decides to, for example, shift guidance device 10 in one direction or another (e.g., up, down, side to side) thus altering the path the bone removal instrument will follow. As guidance device 10 itself cannot be changed intraoperatively, the angle can be adjusted by shifting the position of guidance device 10 per indicia 13. Thus, indicia 13 provides additional guidance for the surgeon before, and/or during the removal of bone from the vertebra.

Figures 3, 4, 5, 6:
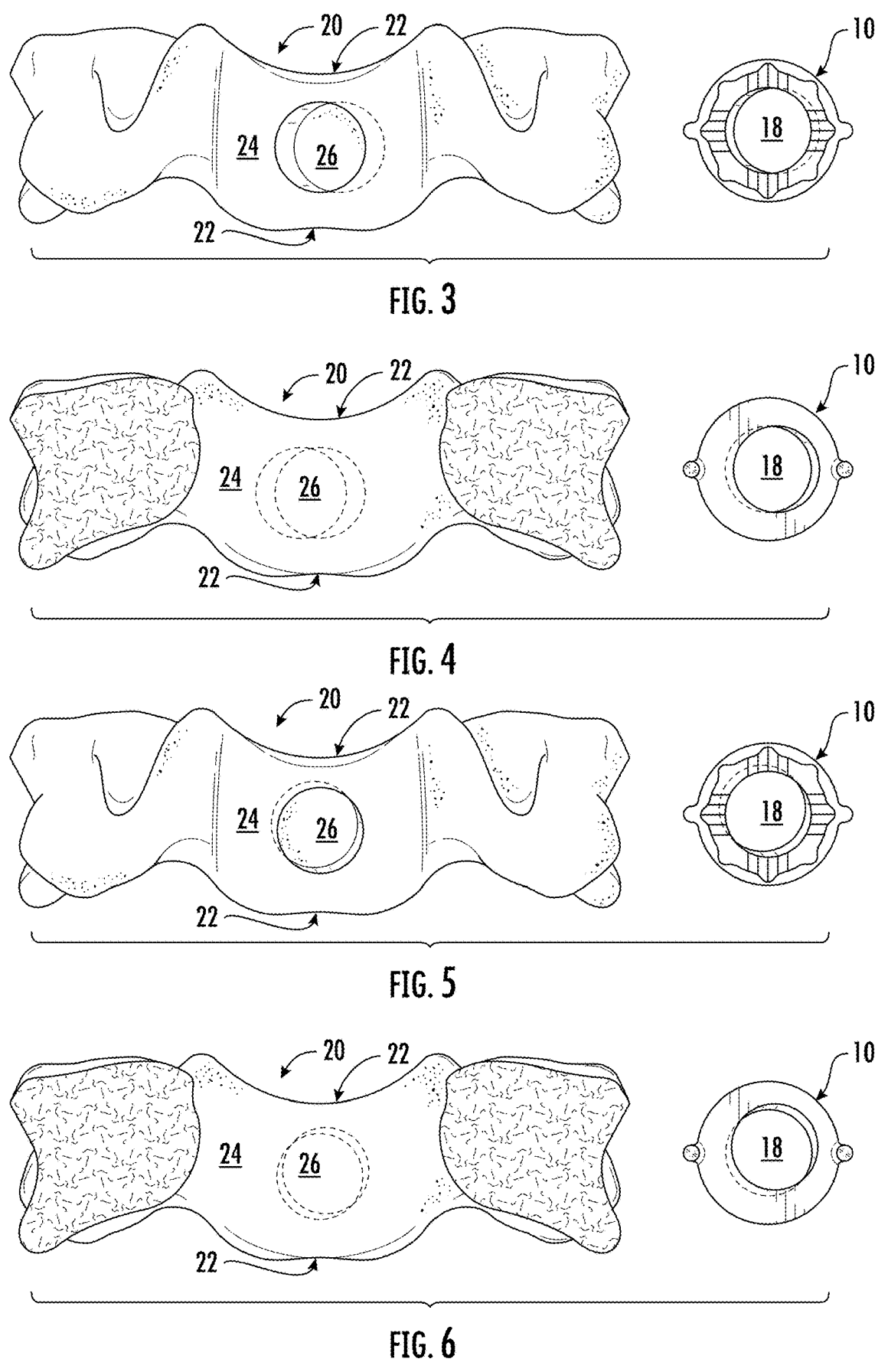

FIGS. 3 and 4 show physical guidance device 10 of the present disclosure and anterior and posterior views, respectively of the cervical vertebra 20 with angled void 26 extending partially through cervical vertebra 20. As described herein, physical guidance device 10 is used to assist a surgeon in guiding a bone removal instrument within a void 26 created in the vertebral body of a cervical vertebra which is a central portion 24 of cervical vertebra 20 between the two endplates 22 of the cervical vertebra 20. In this embodiment, void 26 extends partially through center portion 24 of cervical vertebra 20. In other embodiments, void 26 extends completely through center portion 24. As described herein, a vertebral body replacement device may be placed within void 26 and between endplates 22. In one embodiment, the vertebral body replacement device has been given a PLR product code from the FDA.

As shown in FIGS. 3 and 4, the angled aperture 18 of guidance device 10 has created an angled void 26 partially through vertebral body 20. Thus, FIGS. 3 and 4 show the results of guidance device 10 and an angled aperture 18 of guidance device 10 used to direct the angle of the bone removal instrument in order to create an angled void 26 within cervical vertebra 20.

FIG. 5 is a top view of the physical guidance device 10 of the present disclosure and an anterior perspective view of the cervical vertebra 20 with an alternately angled void 26 partially through the cervical vertebra 20. As can be seen in FIG. 5, the void 26 is angled in a different orientation than the void 26 shown in FIG. 3. Thus, physical guidance device 10 can be used by the surgeon to assist in inserting the bone removal instrument in the cervical vertebra 20 in any variety of different angles, orientations, and depths.

FIG. 6 shows physical guidance device 10 with an angled aperture 18 and a posterior view of cervical vertebra 20 showing the angle of void 26 that was created by the bone removal instrument with the use of guidance device 10.

Figure 7:
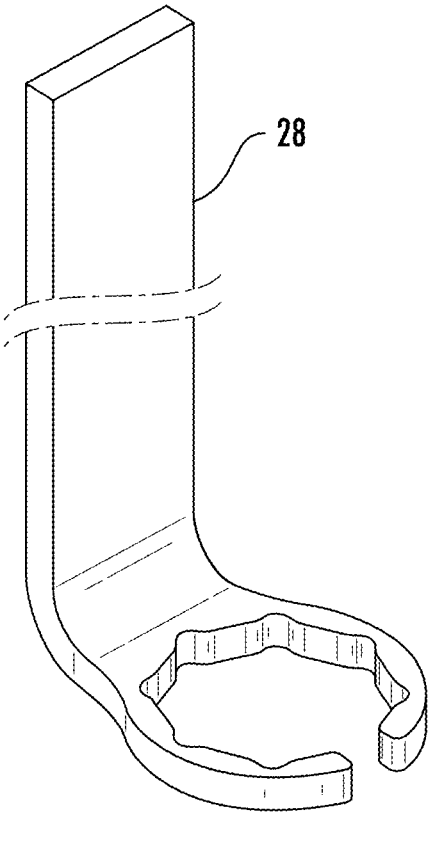
FIG. 7 is a perspective view of a handle to be used with the physical guidance device of the present disclosure.

FIG. 7 is a perspective view of a handle 28, which in some embodiments may be used with physical guidance device 10, as described herein. In one embodiment, handle 28 a detachable handle separate from physical guidance device 10. Handle 28 is used to hold the physical guidance device 10 and apply downward pressure or other holding functions.

FIG. 8 is an axial perspective view of physical guidance device 10 being used to guide a bone removal instrument 30 within the void 26 in cervical vertebra 20. In this embodiment, handle 28 is used to assist the guidance process. As explained herein, the performance of a partial vertebrectomy procedure requires a complex range of angles, single and compound, and depth and length characteristics for the surgeon to consider, which generally depends on the pathologies that are addressed by the partial vertebrectomy procedure. Advantageously, and as can be seen in FIG. 8 (and FIG. 10), the aperture 18 (not labeled) of guidance device 10 is sized to allow bone removal instrument to be angled during the partial vertebrectomy procedure. Depending upon the angle needed to perform the procedure, the surgeon can select one of a series of guidance devices 10, each with its own uniquely sized and/or angled aperture 18 to properly guide bone removal instrument 30. The guidance device 10 of the present disclosure is not limited to allowing bone removal instrument 30 to be inserted within the guide 10 and in cervical vertebra 20 at only the angle shown in FIG. 8. Depending upon the size and dimensions of guidance device 10 and its aperture 18, bone removal instrument 30 may be guided to enter cervical vertebra 20 with the assistance of guidance device 10 at virtually any angle. Throughout this disclosure, the various exemplary angles that are discussed are defined as angles with respect to the vertical dashed line shown in FIGS. 8-11.

FIG. 9 is an axial perspective view of physical guidance device 10 being used to guide a bone removal instrument 30 part of the way through the void 26 in cervical vertebra 20. In this embodiment, handle 28 is not being used in the guidance process. In both FIG. 8 and FIG. 9, void 26 (not labeled) only extends partially through cervical vertebra 20.

Figure 10:
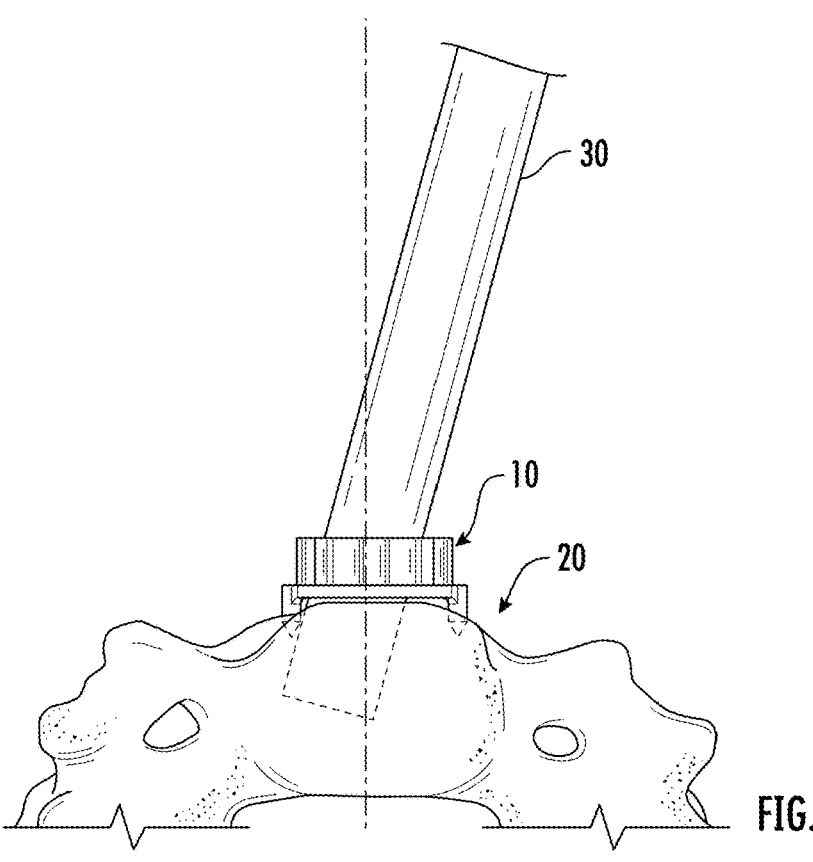
FIG. 10 is an axial view of the physical guidance device of the present disclosure with a bone removal instrument inserted at an angle within a void extending partially within the cervical vertebra.

FIG. 10 is an axial view of physical guidance device 10 and a bone removal instrument 30 inserted at an angle within the void 26 (not labeled) within cervical vertebra 20. Again, the angle taken by bone removal instrument 30 shown in FIG. 10 is exemplary only. The surgeon is free to use one or more guidance devices 10 from a series of guidance devices 10 to assist in the surgical procedure depending upon a variety of factors explained herein. Again, in this embodiment, the void extending only partially within the cervical vertebra 20.

Figure 11:
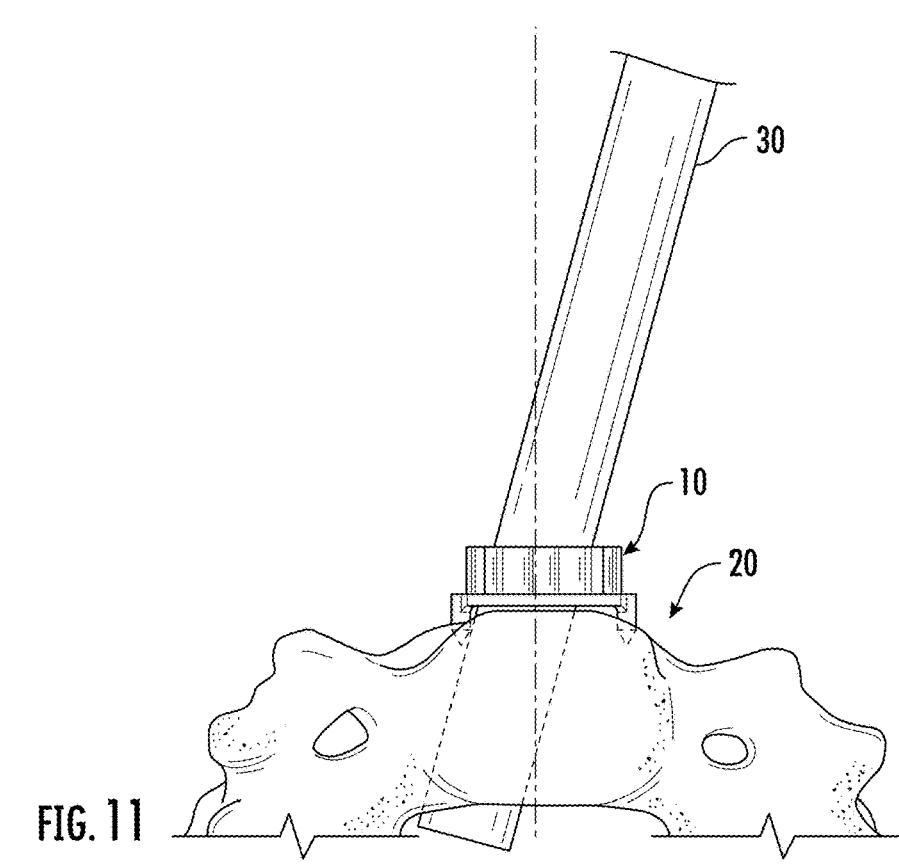
FIG. 11 is a side view of the physical guidance device of the present disclosure partially inserted at an angle within a void extending through the cervical vertebra.

FIG. 11 is an axial view of physical guidance device 10 and a bone removal instrument 30 inserted within the void in cervical vertebra 20. Again, physical guidance device 10 allows bone removal instrument 30 to be inserted within the void at various angles depending on the guide selected, including the exemplary angle shown in FIG. 11. In this embodiment, the void 26 extends completely through cervical vertebra 20, thus allowing bone removal instrument 30 to extend through and out the bottom of cervical vertebra 20.

Figure 12:
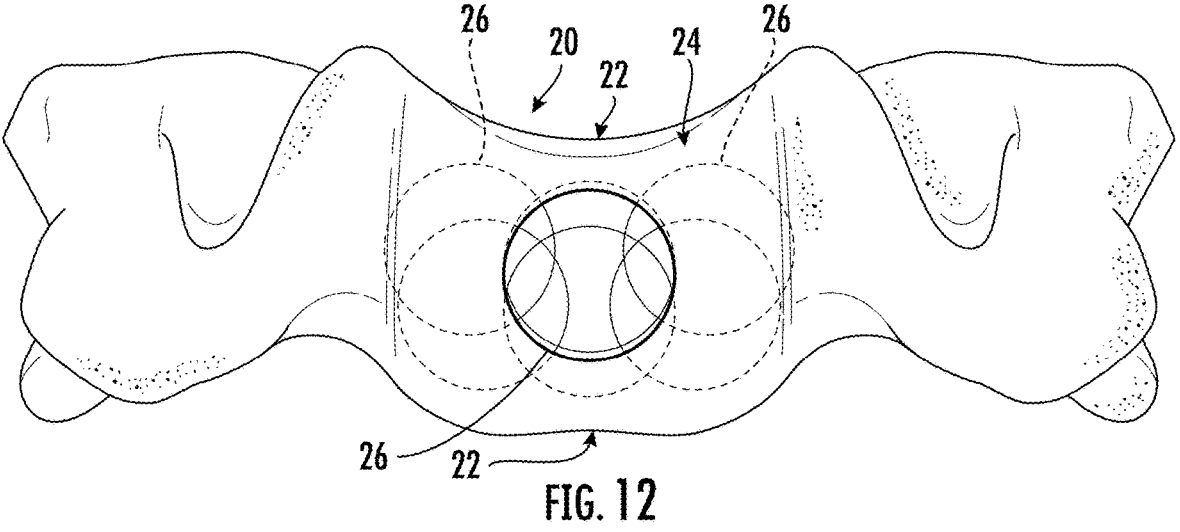
FIG. 12 is an anterior view of the cervical vertebra showing different pathways into the vertebral body achieved by using a selection of guidance devices.
Figure 13:
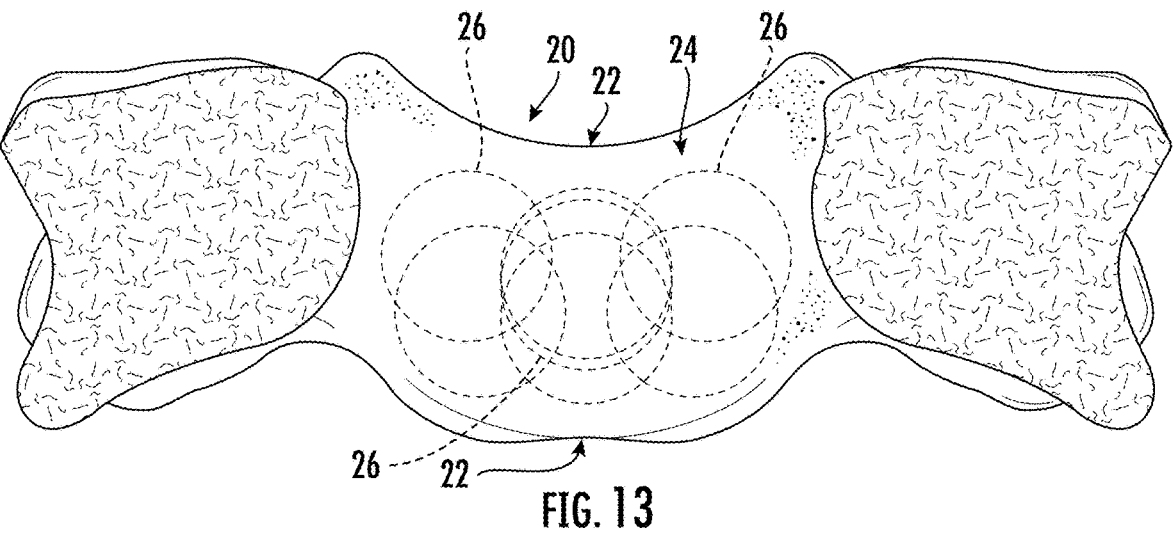
FIG. 13 is a posterior view of the cervical vertebra showing different pathways into the vertebral body achieved by using a selection of guidance devices.

FIG. 12 is an anterior view of cervical vertebra 20 showing different pathways that can be achieved by using a selection of guidance devices 10. FIG. 13 shows a posterior view of the cervical vertebra 20 with the different pathways into vertebral body 20 achieved by using a selection of guidance devices 10. The dark ring in FIG. 12 shows an exemplary starting point on the front of cervical vertebra 20 for all the voids 26. FIG. 13 shows the terminus of each of the channels, i.e. voids 26. Thus, although the starting point is represented by the dark circle, the terminus of each of these voids 26 need not pass all the way through cervical vertebra 20 and can pass through at various angles, at the surgeon's discretion.

In use, the surgeon could create a single angle or a compound angle within cervical vertebra 20 with just a single pass through guidance device 10. This is because, in one embodiment, when manufactured, aperture 18 in guidance device 10 can be drilled as either a single angle or a compound angle. Thus, in use, the surgeon places guidance device 10 on the front of cervical vertebra 20, passes bone removal tool instrument 30 through aperture 18 and the void 26 is created at the surgeon's desired angle in one pass. The surgeon need only choose the depth of void 26 and decide whether to pass the bone removal instrument 30 either part way into cervical vertebra 20 or through cervical vertebra 20.

Figure 14:
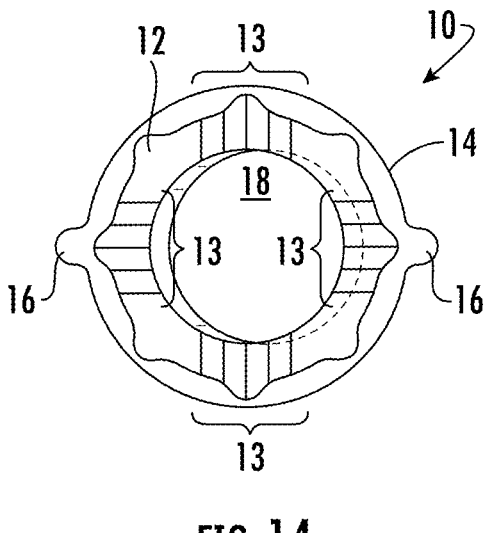
FIG. 14 is a top view of the physical guidance device of the present disclosure with indicia or markings and for insertion at a first angle.
Figure 15:
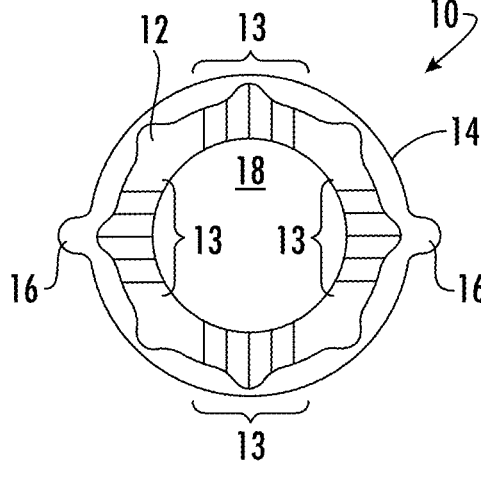
FIG. 15 is a top view of the physical guidance device of the present disclosure with indicia or markings for insertion at a second angle.

FIGS. 14 and 15 represent a top view of physical guidance device 10 showing indicia or markings 13. As shown in FIG. 14, guidance device 10 has an aperture 18 at a particular internal angle. Each guidance device 10 can have an aperture with a particular internal angle to assist the surgeon insert the bone removal instrument at a particular angle in cervical vertebra 20.

It should noted that the arrangement of indicia 13 shown in these figures as well as FIGS. 1 and 2 are exemplary only. Different arrangements of indicia 13 can be used. The primary goal of these markings 13 on the upper portion 12, i.e., visible portion of guidance device 10 is to give the surgeon a reference point to better enable the surgeon to use guidance device 10 during the operative process.

FIGS. 16-19 represent side views of a series of physical guidance device 10, each with varying height profiles. For example, FIG. 16 shows guidance device 10 with a relatively short profile, for example, 6 millimeters or less. In FIG. 17, the height profile of guidance device 10 is higher than the device 10 shown in FIG. 16. Here, the height profile could be, for example, 10 millimeters or less. FIG. 18 shows guidance device 10 with a height profile of, for example, 15 millimeters or less, and FIG. 19 a guidance device 10 with a height profile of, for example, 20 millimeters or less. As seen in FIGS. 16-19, the differences in height profiles could be due to, for example, an increase in height and dimensions of upper portion 12 of guidance device 10 (i.e., the guidance device 10 shown in FIG. 17), an increase in the height and dimensions of platform 14 (i.e., the guidance device 10 shown in FIG. 18), or an increase in the height and dimensions of support legs 16 (i.e., the guidance device 10 shown in FIG. 19). The height profiles and dimensions listed above for each guidance device 10 are exemplary only and other height profiles may be used.

Figure 20:
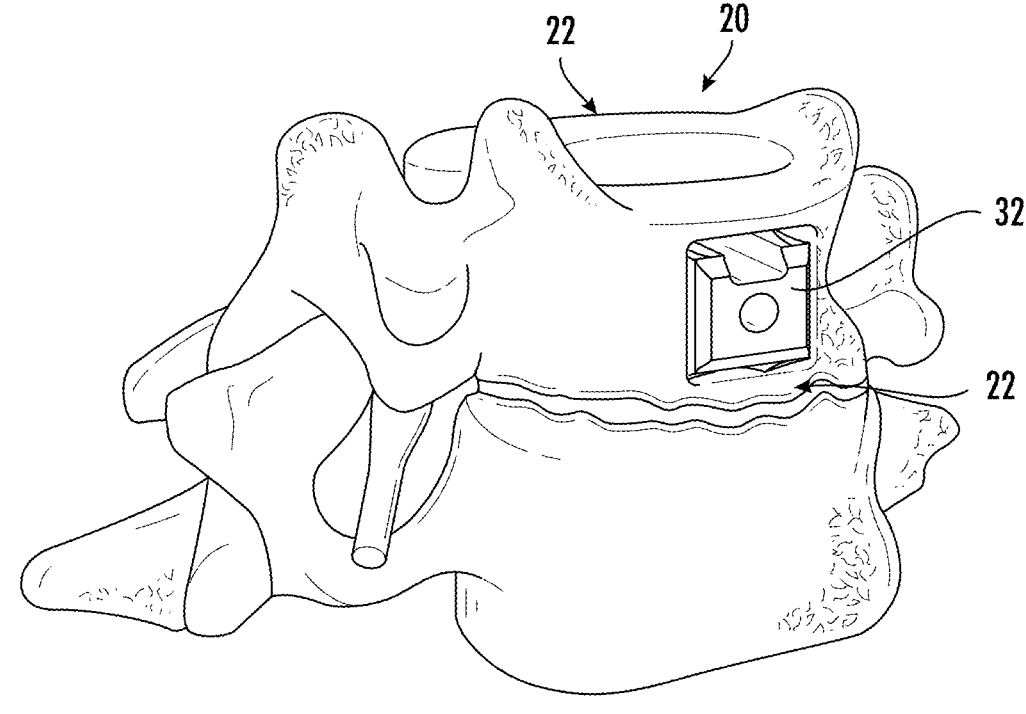
FIG. 20 is a front perspective view of an implant within the void of the vertebral body after the physical guidance device and method of the present disclosure has been utilized.

FIG. 20 shows a front perspective view of vertebral body 20 with an implant 32 inserted therein within void 26. Implant 32 is discussed in further detail below. The use of an implant 32 is optional and is upon the surgeon's discretion.

Disclosed herein is a method of reducing excess bone removal and reducing time in the operating room while improving surgical accuracy and patient outcomes in the performance of a partial vertebrectomy procedure. This disclosure presents an inventive method of planning and performing a partial vertebrectomy procedure and this disclosure includes the necessary device or devices to perform the method. In an anterior cervical spinal surgical procedure called a partial vertebrectomy procedure, a portion of the vertebra must be removed. Prior to this disclosure, when performing a partial vertebrectomy procedure, which is a clearly defined and well understood procedure by those skilled in the art of cervical spine surgery, the surgeon begins by removing an intervertebral disc and then bone until the location of the pathologic bone or tissue is reached. This means that in comparison to the method disclosed in this application, in the cases performed by the current traditional approach, the direction to the pathologic bone or tissue will be indirect. The word "indirect" in this case means, for example, that if the single focal surgical target the surgeon has in mind is in the middle of the vertebral body 20, in accordance with this disclosure, the removal of the intervertebral disc and the vertebral endplate 22 and one half of the vertebral body 20 is unnecessary since this is removed only for access to the middle of the vertebral body 20. In light of inventive method disclosed herein, this would be considered excess bone and tissue removal, not to mention time consuming, since the surgeon is working in direct proximity to the spinal cord. Consequently, this excess bone and tissue removal is not without risk. If the target is in in the center of the vertebral body 20, removing disc tissue, a vertebral endplate 22 and bone purely for access to the center of the vertebral body 20 increases the risk to the patient and decreases the benefit to the patient as well as increasing pain and recovery time. Prior to this disclosure, there has been no alternative.

The methods disclosed in this application describe, in one embodiment, a method of preoperative planning, a surgical method and a physical guidance device 10, or depending on surgeon preference, a series of guidance devices 10 to choose from, in order to make a more direct approach through or into a cervical vertebra 20 towards a surgical target within, upon, or in proximity to, the subject cervical vertebra 20.

In one embodiment, the guidance devices 10 of the present disclosure are single-use and/or disposable guidance devices 10.

In another embodiment, the guidance devices 10 of the present disclosure are custom made, i.e., made-to-order guidance devices.

In another embodiment, the guidance devices 10 of the present disclosure are prescription devices, i.e., a prescription is required to purchases the guidance devices 10.

As will become apparent in the detailed description of this inventive method of performing a partial vertebrectomy procedure, this procedure attempts to, in addition to minimized bone, endplate, and disc removal, also minimize or avoid altogether the retraction of delicate soft tissues such as the longus colli muscles. Retraction of the longus colli muscles is performed routinely and without much consideration, as current surgical methods do not provide an alternative prior to this disclosure.

The methods of this disclosure allow a surgeon to avoid the need to perform the excess bone, endplate and disc removal that requires the use of a cervical plate and fusion when avoiding this is determined by the surgeon to be in the patient's best interest. While those schooled in the art of anterior cervical spine surgery take the placement of an anterior cervical plate for granted, a reading of the steps involved in the placing of the plate reveals a time-consuming procedure that is not without short- and long-term risk to the patient. The drilling of screw holes and the plating procedure has been going on for a long period of time and it has become a natural and necessary step in anterior cervical spine surgery. But in view of the methods and devices of this disclosure, it no longer has to be.

The following will illustrate several use-cases of the methods and apparatuses of the present disclosure.

In accordance with one embodiment, the method of the present disclosure will typically begin with an image study (CT scan, MRI Scan, X-Rays, or any combination of these). The combined image studies are analyzed by a skilled radiologist and a qualified orthopedic or neuro-spine surgeon skilled and trained in anterior cervical spine surgery. The surgeon will then compare the symptoms disclosed by the patient to what is revealed in the image studies and the radiologist's report.

In this embodiment, we will use, as an example, a small abnormal bone growth called osteophyte which is a bony excrescence (any abnormal growth from the surface of a part) or outgrowth of bone. The osteophyte, in this example, is compressing the neural anatomy and causing the patient to suffer pain and weakness in the extremities. In accordance with the methods and apparatuses in this disclosure, instead of planning to automatically remove an intervertebral disc, vertebral endplates 22, and a large portion of the vertebra 20, the surgeon will as part of the preoperative planning of the present disclosure to minimize excess bone removal, the surgeon will use a surgical planning software to measure the angles or angulation from the point of entry to the desired ultimate point of contact with the surgical target. With this method, the surgeon may prefer use a template or a simple manual instrument to measure the distance and the angle of the surgical target, the osteophyte in this case, in relation to a point on the front of the vertebral body selected for entry.

At this point, using the software or a static image, the surgeon will track or map out the point of the pathology, the osteophyte, and to the ideal point on the vertebral body 20 in which the surgeon could enter the vertebral body 20. With the angles noted, the surgeon measures the distance from the clinically ideal entry point to the point of contact to the osteophyte (target). In this example, we will say the distance is approximately 15 millimeters. Next, the surgeon measures the angle of the most clinically ideal entry point upon the vertebral body 20 and trace it back to the osteophyte. At this point, the surgeon will closely assess the angle of the chosen approach path. In this example, we will say the angle is 14 degrees. In some cases, it may very well be a compound angle but for this example we will say a simple 14-degree approach with a depth of 15 millimeters is ideal.

Disclosed herein is a physical guidance device 10. In this disclosure, a physical guidance device 10 is differentiated from an image guided device. An image guidance device is a method of guidance using one or more computers and one or more images obtained by radiological methods, i.e., X-Ray, MRI, CT, etc., and merging such image or images onto one or more computer screens with a computer-generated image of an instrument or an implant. When the radiologic images are merged together with a computer-guided image of an instrument or an implant which is tracked in the operating room by computers and/or camera arrays, the combined images can be used as a method of guidance for a surgeon.

In one preferred embodiment disclosed herein, physical guidance device 10 is provided wherein the surgeon relies upon the physical guidance device 10 to direct the pathway of the bone removal instrument 30. In this embodiment, the surgeon may use intraoperative radiological methods such as an X-Ray to confirm or follow bone removal instrument 30 but this is following the physical bone removal instrument 30 and not a virtual image generated solely by a computer array tracking the instrument.

Physical guidance device 10 of the present disclosure physically guides bone removal instrument 30 along a direction selected by the surgeon for the surgery. The surgeon may use or may not use a form of intraoperative radiology such as X-Ray to follow the progress of the bone removal instrument 30 but with or without X-Ray imaging, physically guiding a bone removal instrument 30 is distinctly different than utilizing a virtual computer-based image guidance system. While the physical guidance device 10 of the present disclosure is not connected directly to a computer or any type of guidance system, a surgeon may be free to provide a separate bone removal tool that may or may not be connected to other virtual guidance systems.

In this example, the surgeon uses guidance device 10 that has, for example, a 14-degree guide angle in the direction the surgeon has requested from his pre-operative analysis and planning. Furthermore, the surgeon will request a bone-removal instrument 30 dimensionally compatible with this guidance device 10, for example, a trephine, or another bone removal tool which may or may not be associated with this guidance device 10. In the present example, the surgeon will set a depth for the bone removal tool of, for example, 15 millimeters. The surgeon will then place the selected guidance device 10 upon the anterior facing surface or anterolateral surface of the vertebral body. The guidance device 10 provides a direct line of direction and guidance of depth for the removal of bone, i.e., the partial vertebrectomy procedure.

At this point, the surgeon will use a bone removal instrument 30, and with the aid of guidance device 10 and the bone removal instrument 30 selected by the surgeon, the surgeon will pass into the vertebral body 20 from the point of entry selected during the pre-operative planning stage and continue on into the vertebral body 20 removing bone and therefore performing the partial vertebrectomy procedure as the bone removal tool passes into the vertebral body 20 toward the surgeon's target.

When the surgeon's bone removal tool arrives at the selected target, the partial vertebrectomy procedure has been performed. If, at this point, the partial vertebrectomy procedure itself has not completely removed the surgical target, i.e., in this example, the osteophyte, the surgeon may remove any remaining osteophyte and begin to conclude the surgery at this time. The surgeon may decide to use an implant 32 or not to use an implant 32 depending upon the surgeon's determination of the patient's bone quality and of the state of the vertebral body 20 at the end of the bone-removing partial vertebrectomy procedure. Regarding the depth of the partial vertebrectomy procedure or the targeted pathology, the surgeon may pass all way through the vertebral body 20 if necessary or stop before passing through the vertebral body 20. These decisions are made at the surgeon's discretion as to what is in the patient's best interest and what increases the benefit of the procedure to the patient and what reduces risk to the patient. The result in the example above is that the partial vertebrectomy procedure was performed by the surgeon with directional precision only removing a portion of bone in the smallest diameter required by the pathologic surgical target as determined by the surgeon. The intervertebral disc and end plates 22 and the rest of the vertebral body 20 remain intact.

In another example, a surgical target prompting the performance of the partial vertebrectomy procedure may be one of the other pathologies listed in the indications for use for a partial vertebrectomy procedure where the surgical target may be located within or near the center of the vertebral body 20. In this case, the surgeon would ideally preoperatively plan the trajectory into the vertebral body 20 beginning at the anterior or anterolateral starting point with a bone removal plan intended to stop in the center or near-center of the vertebral body 20.

Instead of automatically removing the intervertebral disc and then beginning to remove bone by necessarily beginning at the top or bottom of the vertebral body 20 where an intervertebral disc has been removed, the method and device of this disclosure allows the surgeon, when beneficial to the patient, to begin and complete bone removal using the shortest pathway possible from outside the vertebral body 20 and into the vertebral body 20 and halting at the point in which the surgical target has been removed. This would include a surgical target within and/or without the subject vertebral body 20.

When the method and device of this disclosure are used in the performance of a partial vertebrectomy procedure, the result is that the minimum amount of bone will be removed, the minimum amount of retraction of soft tissue will be used, and the minimum amount of time will be required and, in many cases, the intervertebral discs and the vertebral endplates 22 will be functionally preserved. This result is a partial vertebrectomy procedure that does not begin with the removal of intervertebral disc and end plate 22. This method will permit the surgeon to preserve the functional aspects of the intervertebral discs and the vertebral endplates 22 even if a small amount of disc and/or endplate 22 are removed or manipulated. Leaving the intervertebral discs and vertebral endplates 22 functionally intact will reduce patient recovery time and preserve motion for the patient's spinal segment.

By utilizing the present disclosure, a partial vertebrectomy procedure may be performed with greater accuracy, which will reduce unnecessary bone removal and limit bone removal to the surgeon's determination as to what is in the patient's best interest. What is described herein is a method of performing a procedure called a partial vertebrectomy procedure that creates a bone removal procedure directed toward a patient's particular need. Therefore, unlike following a manufacture's recommendation for ideal application and use of an implant 32, the surgeon will be following a patient's clinical needs and the amount of bone removed and the direction of removal will be based upon the surgeon's determination of the patient's need and best interest. This means the surgeon will use this method to remove a widely varying amount of bone and using supplied disclosed devices which will provide the surgeon guidance with a number of different angles of approach to the surgical target.

In the example above of the surgeon desiring to reach a pathological target at the center of the vertebral body 20, during the planning phase, the surgeon will have a variety of image options available from many different sources such as CT scan, MRI, etc., to review two-dimensional or computer-generated three-dimensional images of the cervical vertebral body 20 the surgeon wants to enter. The surgeon will select the preferred or ideal point of entry and measure the distance to the target which will be the termination point, in this case example, the center of the vertebral body 20. The surgeon will also measure the angle or compound angles from the entry point to the termination point. By carefully studying the entry point and the termination point, the surgeon will be able to determine the precise distance to be traveled and the single angle or compound angle to follow to arrive at the targeted point. The surgeon will select guidance device 10 of this disclosure that matches or most closely matches the angle the surgeon determined was optimal for the patient's partial vertebrectomy procedure. It is intended that the surgeon will chose from a variety of guidance devices 10, where the guidance devices 10 may include single angles, compound angles, or no angles. Surgeons have personal preferences that must be respected and patients have widely varying anatomy and pathologies. For this purpose, it is intended that a wide variety of guidance devices 10 will be provided in a series to match the needs of both patient and surgeon. Some guidance devices 10 will be simple whereas others may be complex and include computer assisted image guidance with images updated intraoperatively as the complex procedure progresses. This disclosure anticipates custom guidance devices 10 being made for patients where the surgeon determines a custom guidance device 10 would provide a benefit to the patient undergoing a partial vertebrectomy procedure.

The present disclosure introduces guidance devices 10 and methods of use to be used for partial vertebrectomy procedures upon the anterior cervical spine. The guidance devices 10 disclosed herein may be pre-configured, or pre-configured in a series, may include electronics with or without computer/software capabilities, and/or may be mechanical.

Some partial vertebrectomy procedures are rather straight forward while other partial vertebrectomy procedures are more complex. The intent of the present disclosure is to provide guidance devices 10 and uses of these guidance devices 10 to suit the preferences of the surgeon as well as the needs of each patient. The disclosed method of providing guidance devices 10 and methods of use to the partial vertebrectomy procedure will allow this otherwise ignored procedure to enter into the family of procedures that are considered minimally disruptive and/or minimally invasive. Providing the disclosed guidance method will permit a surgeon to customize the pathway to the patient's pathology by pre-operative analysis revealing the most direct or otherwise least disruptive pathway to the patient's surgical target. This is in contrast to the partial vertebrectomy of today that follows the routine of first removing the intervertebral disc, then removing the vertebral endplate 22, and then systematically removing portions of the vertebral body 20 until the surgical target is reached. Having a guidance device 10 and a guidance methodology that provides a trajectory directly to the surgical target through the shortest path will reduce excess bone, vertebral endplate 22, and disc removal and will speed up patient recovery along with the surgery itself.

In another exemplary use case, the surgeon has a target internal to the vertebral body 20, posterior and lateral to the center, and the surgeon has decided that an ideal point of entry into the vertebral body 20 is centered on the front of the vertebral body 20. To perform the partial vertebrectomy with minimal bone removal by using this disclosed method, the most direct access might be achieved be by using a guide set at, for example, a primary angle of approximately 17 degrees and a secondary angle of approximately 8 degrees (i.e., 17°×8°) and to a depth of 13 mm). After the performance of the exemplary partial vertebrectomy procedure within the vertebral body 20, the surgeon determines whether or not to place implant 32 into the space created by the removal of bone, i.e., the partial vertebrectomy procedure. This determination made by the surgeon depends on numerous factors such as, for example, bone quality, volume of removed bone, pathology of the target, presence of or risk of infection, among others. If a surgeon is to perform a partial vertebrectomy procedure within a cervical spine, the surgeon may have many options for implant sizes etc., but any implant 32 placed during a partial vertebrectomy procedure within a cervical spine must necessarily include a PLR product code from the FDA. This means the implant 32 has been disclosed, tested, and validated as a partial verte-brectomy procedure implant called a Partial Vertebral Body Replacement Device. If implant 32 does not have a PLR product code from the FDA this necessarily means the device is not a Partial Vertebral Body Replacement Device. It may be many other things but it is not a vertebral body replacement device for placement during the performance of a partial vertebrectomy of a vertebral body 20 resected or excised for the treatment of tumors, trauma/fracture, or osteomyelitis, or to achieve decompression of the spinal cord and neural tissues in cervical degenerative disorders.

The present disclosure relates to guidance devices 10 and methods that are used for a specific procedure, namely a partial vertebrectomy procedure performed upon an anterior cervical spine. The performance of a partial vertebrectomy procedure will require a complex range of angles, single and compound, and depth/length characteristics specific to the variety of pathologies that are addressed by a partial verte-brectomy procedure. As the method of guidance and the guidance devices 10 disclosed herein are not paired to a specific implant 32 or set of implants 32, the range of guidance devices 10 must necessarily be matched to the variety of pathologies that exist in the cervical spine that can be treated by the performance of an anterior cervical partial vertebrectomy procedure. This includes requiring a variety of dimensions such as diameters, widths and heights, in addition to the angles, compound angles, trajectories, and lengths/depths to address the needs a surgeon may have when performing an anterior cervical partial vertebrectomy procedure. As disclosed previously, the range of pathologies that may be addressed by a partial vertebrectomy procedure and the methods of performing such procedure may include, per the FDA, as described in the indications for use of the partial vertebrectomy procedure vertebral body replacement device, partial vertebrectomy of a vertebral body 20 resected or excised for the treatment of tumors, or trauma/fracture, or osteomyelitis, or to achieve decompression of the spinal cord and neural tissues in cervical degenerative disorders.

It is understood why an anterior cervical partial verte-brectomy guidance device 10 has not previously been made available. Guidance devices usually require the attachment of reference devices, or possibly an implantable device in order to function as a reference device, in proximity or upon the area of anatomy requiring guiding reference. The dis-closed guidance device 10 and its method of use can be performed with or without reference devices, while provid-ing guidance to perform the bone removal procedure described as a Partial Vertebrectomy Procedure.

The method and guidance device 10 of the present dis-closure provides benefits such as but not limited to, a reduction in operating time, a reduction in the retraction of the delicate soft tissues anterior to the anterior cervical spine, and a greater accuracy in targeting. Greater accuracy in targeting and therefore accuracy in locating and intraop-eratively reaching the pathology that created the need for surgery in the first place allows for a very important reduc-tion in unnecessary bone removal.

In another exemplary use embodiment, a surgical target that the surgeon must access is off the center of a vertebral body 20 of a cervical spine. Prior to this disclosure, using previously-known methods, the surgeon would, after gain-ing exposure to the spine, begin by removing one of the intervertebral discs adjacent to the vertebra 20 and then begin removing bone from the vertebral body 20 by begin-ning at the endplate 22 (the hard cortical bone that makes up the top and bottom of a vertebral body, which is the vertebra's point of contact to the intervertebral disc prior to removal of said disc) and continuing removing the vertebral body 20 until the target is reached.

Using the method disclosed in this disclosure, the surgeon would first make an image of the patient's vertebral body 20 available for review. This image, depending on the type of pathology and the surgeon's preference could be an X-Ray, an MRI, a CT, or another combined image study. The location of the surgical target will be noted and the preferred entry point of what will become the starting point of a surgical direction into the vertebral body 20 will be selected and noted by the surgeon. This will usually be, but not always, the shortest distance to a targeted pathology within or without a vertebral body 20. For clinical reasons, the surgeon may determine the best approach may be closer to the endplate 22 instead of the shortest distance. The point being the surgeon will choose the optimum route to the targeted pathology. Contrary to the traditional method where the default starting point is the disc and endplate 22, with this disclosure the surgeon has broad new options when choosing the starting point.

In accordance with the methods disclosed herein, the surgeon will have the ability to mark out the target, the optimum entry point, and measure the distance and angle from the entry point to the target. This will now become the optimum trajectory to the pathologic target. For this example, the surgeon may desire to enter the vertebral body 20 just above the inferior vertebral endplate 22 and termi-nate the removal of bone directly at the target. At this point, the surgeon will determine the size and shape of the required bone removal. The actual size and shape of bone removal the surgeon creates, i.e., circular, cylindrical, squared, rectan-gular, etc., will vary depending upon clinical requirements of the patient and surgical preferences of the surgeon.

In this exemplary use case, the surgeon chooses a cylin-drical pathway. The surgeon now has an entry point, a termination point, and a shape of the pathway needed. Next, the surgeon will determine the diameter of the pathway. For this example, the surgeon chooses an eight-millimeter (8 mm) diameter, although the surgeon can choose any diam-eter that best benefits the patient.

Having determined the preference is to enter close to the inferior endplate 22, the surgeon will now determine where in the front of the vertebral body 20, close to the endplate 22 will be the ideal point of entry. For this example, the surgeon finds the center of the front of the vertebral body 20 one millimeter (e.g., 1 mm) just above the inferior endplate 22 because this pathway will require the minimum of retraction of soft tissue including leaving the longus colli muscle in place, helping reduce post operative pain and discomfort which reduces post operative need for pain medications and a shortened recovery timeline.

The surgeon will then map out an approximately 8 mm cylindrical pathway from the center of the vertebral body 20, beginning approximately 1 mm above the inferior endplate 22 to the surgical target. The surgeon then measures the distance from the entry point to the desired target within the vertebral body 20. In this example, the target is within the vertebral body 20 and the distance from the point of entry to the target is approximately 9 millimeters. Using the method of this disclosure, the surgeon determines the pathway from the entry point at the centerline of the vertebral body 20 approximately 1 mm above the inferior endplate 22 with an approximately 8 mm diameter and will need to pass through the vertebral body 20 at a ten-degree (+10° degree) angle for a distance of approximately 9 mm. At this point, the surgeon will be confident that an 8 mm diameter pathway, beginning 1 mm above the inferior endplate 22 at the center of the vertebral body 20 directed at a +10° angle for a distance of 9 mm will put the surgeon directly upon the surgical target within the vertebral body 20 with the absolute minimum required bone removal and soft tissue retraction. Targets can be located within a vertebral body 20, upon a vertebral body 20 as in a mass growing on a vertebral body 20, or a target may be located beyond the vertebral body 20. In this example, the target will is described as being at the terminus of the guided removal of bone. This means the removal of bone, i.e., the performance of the partial vertebrectomy procedure, captures the surgical target and allows the surgeon to successfully conclude the surgery and begin closing the case.

In this disclosure, a series of guidance devices 10 is provided to assist the surgeon in the performance of the disclosed method. The disclosed guidance devices 10 form part of a series of directional guidance devices 10 that the surgeon can choose from to create the desired pathway. The guidance devices 10 can take various forms, thus allowing for variances in surgeon preference and patient-related variables.

In another example, after gaining surgical access to the anterior cervical spine, the surgeon will ask for an 8 mm diameter cutting device and a guidance device 10 with a +8° angle. With the +8°-angle guidance device 10 and the 8 mm diameter cutting device, the surgeon will cut a pathway into the vertebral body 20 12 mm in length from the point of entry. The surgeon will then perform the treatment upon the surgical target and then terminate the surgery.

It is possible that the surgeon determines it is in the patient's best interest to repair the surgical pathway of removed bone, in which case the surgeon would choose from a variety of PLR vertebral body replacement devices from various manufacturers, or the surgeon may determine it is in the patient's best interest not to repair the surgical pathway of removed bone and allow the bone to heal without an implant 32. It is important to note that if a partial vertebrectomy procedure is performed and a manufacturer or provider of implants 32 wants to label the procedure and implant 32 as such, promote or teach the repair of the partial vertebrectomy void, the FDA requires the implant 32 to be officially designated a vertebral body replacement device with an official PLR product code from the FDA. For an implant manufacturer to promote or teach the use of a non-PLR implant would be in direct violation of FDA rules and requirements and laws and regulations. If implant 32 does not have a PLR product code from the FDA, implant 32 is not a vertebral body replacement device. A vertebral body replacement device is the only device that can be used for the repair of a vertebrectomy or a partial vertebrectomy.

Patient bone quality and potential for bone growth to repair the surgical bone removal void by regrowing bone varies from patient to patient and opinions and preferences vary from surgeon to surgeon. Disclosed herein is a method for carefully determining an optimum pathway to a surgical target within or around a cervical vertebral body and providing guidance devices 10 to aid the surgeon in performing a less destructive partial vertebrectomy procedure. The performance of such a partial vertebrectomy procedure has never been performed and is counterintuitive. The performance of a partial vertebrectomy procedure is associated with a comparably unrefined removal of bone, and bone removal only after the removal of an intervertebral disc. In this partial vertebrectomy procedure, the surgeon may choose to remove an intervertebral disc or may choose not to remove an intervertebral disc. In this partial vertebrectomy procedure the surgeon is able to determine a more precise removal of bone thus greatly reducing the amount of bone removal required and the amount of tissue retraction required in the performance of the partial vertebrectomy procedure.

Many surgeons and published clinical papers believe the retraction of the soft tissues is often the cause of one of the most common of post operative problems associated with anterior cervical spine surgery; dysphagia. Dysphagia describes the inability to swallow or difficulty in swallowing. This improved procedure and planning method of the present disclosure permits a very strategic analyzation of the amount of bone to be removed, the direction of bone removal, and how to plan bone removal to minimize soft tissue distraction during the performance of a partial vertebrectomy procedure.

It is possible and common that a surgical target of a partial vertebrectomy procedure is not in the center of a vertebral body 20. Surgical targets requiring a partial vertebrectomy procedure vary considerably and may occur anywhere within or without a vertebral body 20. Disclosed herein is a method that can be used for a variety of pathologies requiring the performance of a partial vertebrectomy procedure.

In the present example, the pathology rested in the vertebral body 20. It is possible and even likely the pathology will not reside in the direct center of the body. If the surgical target was in the posterior third of the vertebral body 20 and in the right quarter of the vertebral body 20, the surgeon may need a guidance device 10 that provides a compound angle. As this disclosure describes a selection of guidance devices 10 and methods to address the varying patient needs it is anticipated that a compound angle will be provided for. For example, guidance device 10 could be provided with a cephalad +8° angle with a right +15° angle.

It is anticipated that the performance of the partial vertebrectomy procedure may create a pathway into a vertebral body 20 of the cervical spine or it may create a pathway through a vertebral body 20 of the cervical spine. The pathway may enter the spinal canal the pathway may not enter the spinal canal. The goal of the guidance method and guidance devices 10 disclosed herein are to provide directional guidance to the surgeon during the performance of a partial vertebrectomy procedure in which the procedure requires the removal of bone associated with the partial vertebrectomy. This is unique as the guidance devices 10 provided for this procedure are not necessarily associated with an implant 32 to be attached to or into a vertebral body 20 as is the case with bone plates and associated implants 32. The partial vertebrectomy procedure may be performed independent of an implanted device 32, with the use of implants 32 left to the discretion of the surgeon and independent of the use of the guidance method and device 10 of this disclosure. Furthermore, this disclosure is unique in that it is applied to the partial vertebrectomy procedure and the methods of surgical planning and devices for implementing such a surgical plan are designed specifically for the partial vertebrectomy procedure and to minimize the amount of bone removal performed during the course of such a procedure. Prior to this disclosure, this method and the described guidance devices 10 have not been described, disclosed or used in the performance of a partial vertebrectomy procedure upon an anterior cervical vertebral body 20.

To clarify and formalize the independence and uniqueness of the partial vertebrectomy procedure as being unlike other orthopedic or neurosurgical procedures, as referred to earlier, the FDA has a unique identifier code for implants 32 used during the performance of a partial vertebrectomy procedure. If the method and the guidance devices 10 of this disclosure are to be distributed and taught to be used in conjunction with an implant 32 because the surgeon determined an implant 32 would be beneficial to the patient, the provider would necessarily be required to select an implant 32 that carries the FDA product code PLR. If the surgeon chose a manufactured implant that did not have a PLR product code the surgeon would be using a device off label. The use of the methods and guidance devices 10 of this disclosure do not require the use of an implant 32 for the performance of a partial vertebrectomy procedure but if a partial vertebrectomy procedure is performed and repaired with an implant 32 provided by a manufacturer for repairing a partial vertebrectomy void, the implant must be a PLR implant 32.

For the purposes of this disclosure, the term "cervical spine" follows the usual guidance of the FDA, which when referring to vertebral body replacement devices, includes the second cervical vertebra (C2) through the first vertebra of the Thoracic spine (T1). This is commonly expressed as (C2-T1) which means the second through the seventh cervical vertebrae and the first and most superior of the thoracic vertebrae. In the present disclosure, unless otherwise specified, when discussing implants or implantable devices the term "implantable device" or "device" may be used interchangeably with the terms "implant" or "medical instrument."

The FDA Defines a Vertebral Body Replacement Device as:

Device—Spinal Vertebral Body Replacement device-Cervical

Regulatory Description—Spinal intervertebral body fixation orthosis

Definition—Vertebral body replacement in the cervical spine

Physical State—Metallic or polymeric device (usually rectangular or cylindrical), with open central and lateral canals for bone graft containment, providing rigidity and structural support.

Technical Method—Provides structural support for the indicated population

Target Area—Cervical spine

Product Code—PLR

As described herein, in order for a device to be given clearance to be used as a vertebral body replacement device in the cervical spine and receive the product code PLR from the FDA, the device has to be submitted to rigorous testing. To date, there is not a PLR predicate that has been associated with a guidance method and a guidance device 10 as disclosed herein and this is for fairly direct reasons.

Prior to the guidance methods and guidance devices 10 as disclosed herein, a vertebral body replacement device with a PLR code from the FDA has historically been associated with a broad-based bone removal procedure beginning with the intervertebral disc and vertebral endplates 22. Disclosed herein is a method of preoperative planning and guidance devices 10 that will promote performing a minimally disruptive partial vertebrectomy procedure. The devices 10 and associated methods of its use disclosed herein will allow a surgeon to remove only the necessary amount of bone required to be removed and no more. While an implant 32 is not required to perform a partial vertebrectomy procedure an implant 32 may be used at a surgeon's discretion. Therefore, disclosed herein is a method of performing a partial vertebrectomy procedure upon a cervical vertebral body 20 during the course of performing an anterior cervical surgical procedure to a cervical spine and utilizing guidance device 10 to aid in the creation of the partial vertebrectomy void 26. An implant 32 may be placed into the partial vertebrectomy void 26, wherein the implant 32 has received a PLR code from the FDA.

With the introduction of guidance devices 10 to the partial vertebrectomy procedure as disclosed herein comes the ability to introduce a multi-aperture method of performing the partial vertebrectomy procedure. The introduction of the guidance devices 10 and methods of this disclosure allows the surgeon greater precision in the preoperative planning and performance of the surgical procedure. This can allow as surgeon to create one pathway to a pathology and an additional pathway or pathways to other pathologies or for example the introduction of additional instruments to treat one or more pathologies. A simplified example of this would be the placement of a second partial vertebrectomy void 26 next a first void 26 or directed to the terminus of the first void 26. This second void 26 could be used for the introduction of an endoscope for greater visualization or an instrument for the treatment of the surgical target. Surgical planning as disclosed using the methods disclosed herein can allow for the introduction of one, two, or several partial vertebrectomy voids 26 into a cervical vertebral body 20 for the treatment of a pathologic tissue or a target a surgeon has determined should be removed. These singular or plural voids 26 may be repaired or may not be repaired, or one or more may be repaired while one of more is not repaired based upon the decision of the surgeon. The partial vertebrectomy void or voids 26 may be created into the vertebral body 20 of the cervical spine or they may be created through the vertebral body 20 or a combination of both.

The introduction of multiple apertures or voids 26 allows for separate partial vertebrectomy voids to be created. The most anterior aspect of a cervical vertebral body 20 is considered by many to be the area of the vertebral body 20 to carry the greatest loads and therefore maintaining anterior integrity can be a preference for some surgeons. Multiple apertures 26 created through the front of the vertebral body 20 could converge posteriorly creating a larger void 26 close to the spinal canal while having smaller voids 26 in the anterior portion of the vertebral body 20.

Another option anticipated with this method and guidance devices 10 with single and compound angles would allow for more than one partial vertebrectomy void 26 to be created using a second angle guide using the same entry point on the front of the body 20. This would maintain a greater percentage of the integrity of the anterior aspect of the vertebral body 20 will creating more room at the terminus of the void 26, or the combined voids 26. This and other methods become possible by the unique method of preoperative planning and use of the guidance devices 10 of this disclosure. The planning and precision gained by using guidance devices 10 allows for very precise creation of the partial vertebrectomy void or voids 26. The placement of the entry points along with the angle and often angles of the partial vertebrectomy voids 26 allows for the introduction of new options for the surgeons.

This disclosure also introduces a new type of guidance device 10 for use in the anterior cervical spine for the performance of the partial vertebrectomy procedure. In one embodiment, guidance device 10 has lower profiles with single angle and in other embodiments, compound angles. These may be provided in a series of guide devices 10 with a selection of guide devices 10 for the surgeon to choose from based upon the surgeons preoperative planning associated with the performance of the disclosed partial vertebrectomy procedure. In one embodiment, it is anticipated that a unique detachable handle 28 as shown in FIG. 7 may be provided where the handle 28 is separate from the guidance device 10 and the guidance function is uniquely performed within the guidance device 10 separate from the handle 28. If handle 28 is used, it is used to hold the separate guidance device 10 and apply downward pressure or other holding functions. In one embodiment, guidance device 10 may contain a single angle or compound angles wherein the guidance device 10 has a profile of height that is less than twenty millimeters, a profile of height that is less than fifteen millimeters, a profile of height that is less than ten millimeters, and a profile of height that is less than six millimeters.

The handle 28 used with guidance device 10 is a separate instrument that may or may not be used at the surgeon's discretion. This is because different than other directional bone drill guide devices for use in bone related surgery, the angle of direction is performed or directed within the instrument itself. Thus, the outside dimensions of the guidance device 10 including the angles and outside features of the device 10 remain unchanged as does the angle if placement upon the bone. The internal aspect of the guidance device 10 contains the angle or angles. This allows for lower profiles of height than is typically used in a bone application, particularly the anterior cervical spine. This also allows for handle 28 to be in some embodiments attached, and in some embodiments not attached to guidance devices 10 with significantly different angle presentations because the angles are internal to the guidance device 10 and the external dimensions of this embodiment remain constant.

This also allows for custom angles to be requested by a surgeon. The guide blanks may be mass produced with all the devices 10 carrying the same external dimensional characteristics with the internal guidance angle or angles placed into the guide device 10 as requested by a surgeon for a patient need. In one example, a circular guidance device 10 may be provides with an outside diameter of approximately fourteen millimeters and a profile of height of just over six millimeters. This provides an internal area in which to place the angle or angles for the bone removal instrument 30 to follow as the partial vertebrectomy procedure is performed.

Ideally, care is given to minimize the size of the incision and exposure created to access the anterior cervical spine in addition to limiting the retraction of the soft tissues during the anterior cervical spine surgery. For this reason, a range of low-profile and/or low-mass and/or low-bulk guidance devices 10 for use in performing a partial vertebrectomy procedure are herein disclosed. As different patients have different needs and different surgeons have different preferences, a series of more than one guidance device 10 having differing angles and differing height profiles is herein disclosed. Some surgeons will prefer a low-mass or low-profile guidance device 10 in order to avoid disrupting adjacent tissues or obstructing clear visualization for example. Therefore, it is anticipated and disclosed herein that the guidance device 10 of this embodiment may be presented as part of a series of guidance devices 10 which may provide a range of directional angles and may contain a range of different height profiles.

Disclosed herein, in one embodiment, is a guidance device 10 for use in the performance of a partial vertebrectomy of a cervical vertebra during the performance an anterior cervical spinal surgical procedure, wherein the guidance device 10 has a height profile of less than 20 millimeters. A height profile for the purpose of this disclosure is defined as the measurement of the guidance device 10 from the underside of the guidance device 10 which is placed upon the cervical vertebral body 20 to the highest point of height of the guidance device 10.

Also disclosed herein, in one embodiment, is a guidance device 10 for use in the performance of a partial vertebrectomy of a cervical vertebra 20 during the performance an anterior cervical spinal surgical procedure wherein the guidance device 20 has height profile of less than 15 millimeters.

Also disclosed herein, in one embodiment, is a guidance device 10 for use in the performance of a partial vertebrectomy of a cervical vertebra 20 during the performance an anterior cervical spinal surgical procedure wherein the guidance device 10 has height profile of less than 10 millimeters.

Also disclosed herein, in one embodiment, is a guidance device 10 for use in the performance of a partial vertebrectomy of a cervical vertebra 20 during the performance an anterior cervical spinal surgical procedure wherein the guidance device 10 has height profile of less than 6 millimeters.

Disclosed herein, in one embodiment, is a series of guidance devices 10 for use in the performance of a partial vertebrectomy of a cervical vertebra 20 during the performance an anterior cervical spinal surgical procedure where the guidance devices 10 provided in the series of guidance devices 10 can offer a range of variations including various angles and/or height profiles. The surgeon is able to select one or more guidance devices 10 from the series of guidance devices 10 provided in this disclosure.

In another embodiment, a handle 28 used to aid in the holding and placing of the guidance device 10 is disclosed, wherein the handle 28 may be a separate instrument and removable from the guidance device 10.

Operatively, it is clear to the surgeon when a partial vertebrectomy procedure will be or has been performed. The FDA also provides guidance by providing indications as to when a PLR implant may be cleared to be used, as PLR implants are indicated only to be used during the performance of a partial or complete vertebrectomy. For example, according to the typical FDA guidance for the use of a PLR device which would mean for a partial or complete corpectomy, the indications would include a vertebral body 20 resected or excised for the treatment of tumors, or trauma/fracture, or osteomyelitis, or to achieve decompression of the spinal cord and neural tissues in cervical degenerative disorders. This is guidance which manufacturers of implants are required to follow and surgeons are very strongly encouraged to follow.

When a surgeon schedules a surgical case, the surgeon will define the case. For example, if a surgeon schedules the case as a partial vertebrectomy, the surgeon will inform the hospital so the hospital can prepare the room and instruments along with adequate time for a partial vertebrectomy. Furthermore, the surgeon and the hospital will preoperatively notify and gain clearance or authorization with which ever organization is paying for the surgery, an insurance company or Medicare for examples. It is possible and not altogether uncommon that a surgeon starts out intending to perform a lesser or smaller procedure than a partial vertebrectomy, but upon conducting the surgical procedure the surgeon may find that a broader procedure such as a partial vertebrectomy is required in order to properly and completely address the patient's condition successfully. When this is the case, the surgeon will, upon completion of the surgical procedure, dictate detailed notes on the surgical case including declaring, defining, and describing the case as a partial or possible a complete vertebrectomy including the use of a PLR implant if one was used. The surgeon's declaration of the surgery being a partial or a complete corpectomy is authoritative as this information will also be reviewed by the hospital and the insurance provider etc., and is formally recorded and officially documented. It is therefore known that when a partial vertebrectomy has been performed and when such a procedure has been performed, the surgeon will formally and, on the record, describe and define the case as a partial vertebrectomy.

The use of the disclosed guidance device 10 for a partial vertebrectomy procedure with the disclosed features will permit the surgery to be completed with less unnecessary bone removal and preservation of the functionality of the vertebral endplates 22 of the subject vertebral body 20 and the functionality of the adjacent intervertebral discs. This provides a direct benefit to the patient.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A guidance device for use in guiding removal of bone from a selected starting point to a selected termination point between endplates of a single cervical vertebra during performance of a surgical procedure to a cervical vertebral body that does not include a fusion to an adjacent vertebra, the procedure including placement of an implant into a void created by the removal of bone between the endplates, the implant having been given clearance from the Food and Drug Administration (FDA).

2. The guidance device of claim 1, wherein the guidance device is part of a series of guidance devices, and at least one guidance device is selected from the series of guidance devices.

3. The guidance device of claim 1, wherein the guidance device may contain a single angle or compound angles.

4. The guidance device of claim 1, further comprising a handle feature, wherein the handle feature is a separate instrument and is removable from the guidance device.

5. The guidance device of claim 1, wherein the guidance device has a height profile of less than 20 millimeters.

6. The guidance device of claim 1, wherein the guidance device further comprises indicia, the indicia providing additional guidance for a user.

7. The guidance device of claim 1, wherein the implant has been given a PLR product code from the FDA.

8. The guidance device of claim 1, wherein the guidance device can be computer assisted image guidance.

9. A guidance device for use in guidance of a bone removal tool in performance of an anterior cervical surgical procedure that includes placing an implant into a void between two vertebral endplates of a single vertebra in a cervical spine, the implant having been given clearance from the Food and Drug Administration (FDA), wherein the performance of the surgical procedure to the cervical vertebral body results in leaving adjacent intervertebral discs functionally intact and does not include a fusion to an adjacent vertebra.

10. The guidance device of claim 9, wherein the guidance device is part of a series of guidance devices, and at least one guidance device is selected from the series of guidance devices.

11. The guidance device of claim 9, wherein the guidance device may contain a single angle or compound angles.

12. The guidance device of claim 9, further comprising a handle feature, wherein the handle feature is a separate instrument and is removable from the guidance device.

13. The guidance device of claim 9, wherein the guidance device further comprises indicia, the indicia providing additional guidance for a user.

14. The guidance device of claim 9, wherein the implant has been given a PLR product code from the FDA.

15. The guidance device of claim 9, wherein the guidance device can be computer assisted image guidance.

16. A guidance device for performing a multi-aperture surgical procedure to a vertebral body of a cervical spine during performance of an anterior cervical spinal surgery that does not include a fusion to an adjacent vertebra, the multi-aperture surgical procedure including creating a first void in the vertebral body, the first void having an entrance and a terminus region, creating at least a second void in the vertebral body of the cervical spine where the first void was created, and placing at least one implant into at least one of the first void and the second void created in the vertebral body of the cervical spine during the performance of the anterior cervical spinal surgery, the implant having been given clearance from the Food and Drug Administration (FDA).

17. The guidance device of claim 16, wherein the guidance device is part of a series of guidance devices, and at least one guidance device is selected from the series of guidance devices.

18. The guidance device of claim 16, wherein the guidance device may contain a single angle or compound angles.

19. The guidance device of claim 16, further comprising a handle feature, wherein the handle feature is a separate instrument and is removable from the guidance device.

20. The guidance device of claim 16, wherein the guidance device further comprises indicia, the indicia providing additional guidance for a user.

21. The guidance device of claim 16, wherein the implant has been given a PLR product code from the FDA.

22. The guidance device of claim 16, wherein the guidance device can be computer assisted image guidance.

23. A guidance device for use in an anterior cervical spinal surgical procedure that does not include a fusion to an adjacent vertebra, the guidance device being used for guiding removal of bone from a selected starting point to a selected termination point during performance of surgical procedure to a cervical vertebral body, the procedure including placement of an implant into a void between vertebral endplates of a single vertebra of the cervical spine, the implant having been given clearance from the Food and Drug Administration (FDA).

24. The guidance device of claim 23, wherein the guidance device is part of a series of guidance devices, and at least one guidance device is selected from the series of guidance devices.

25. The guidance device of claim 23, wherein the guidance device may contain a single angle or compound angles.

26. The guidance device of claim 23, further comprising a handle feature, wherein the handle feature is a separate instrument and is removable from the guidance device.

27. The guidance device of claim 23, wherein the guidance device has a height profile of less than 20 millimeters.

28. The guidance device of claim 23, wherein the guidance device further comprises indicia, the indicia providing additional guidance for a user.

29. The guidance device of claim 23, wherein the implant has been given a PLR product code from the FDA.

30. The guidance device of claim 23, wherein the guidance device can be computer assisted image guidance.

* * * * *